(12) United States Patent
Rigsbee et al.

(10) Patent No.: US 12,090,137 B2
(45) Date of Patent: Sep. 17, 2024

(54) SOLID Δ⁹-TETRAHYDROCANNABINOL (Δ⁹-THC) COMPOSITIONS

(71) Applicant: CANNA-CHEMISTRIES LLC, Vincennes, IN (US)

(72) Inventors: Emily Rigsbee, Lafayette, IN (US); David T. Jonaitis, Brookston, IN (US); Nathan Schultheiss, West Lafayette, IN (US); Lloyd Steven Miller, Indianapolis, IN (US)

(73) Assignee: CANNA CHEMISTRIES LLC, Vincennes, IN (US)

( * ) Notice: Subject to any disclaimer, the term of this patent is extended or adjusted under 35 U.S.C. 154(b) by 0 days.

(21) Appl. No.: 17/895,347

(22) Filed: Aug. 25, 2022

(65) Prior Publication Data

US 2022/0409572 A1 Dec. 29, 2022

Related U.S. Application Data

(63) Continuation of application No. 17/575,035, filed on Jan. 13, 2022, now Pat. No. 11,478,447, which is a continuation of application No. PCT/US2021/041992, filed on Jul. 16, 2021.

(60) Provisional application No. 63/053,205, filed on Jul. 17, 2020, provisional application No. 63/154,151, filed on Feb. 26, 2021, provisional application No. 63/154,153, filed on Feb. 26, 2021.

(51) Int. Cl.
| | |
|---|---|
| *A61K 9/19* | (2006.01) |
| *A23L 27/30* | (2016.01) |
| *A23L 33/105* | (2016.01) |
| *A61K 9/16* | (2006.01) |
| *A61K 31/00* | (2006.01) |
| *A61K 31/352* | (2006.01) |
| *A61K 33/00* | (2006.01) |

(52) U.S. Cl.
CPC ............ *A61K 31/352* (2013.01); *A23L 27/33* (2016.08); *A23L 33/105* (2016.08); *A61K 9/1617* (2013.01); *A61K 9/19* (2013.01); *A23V 2002/00* (2013.01)

(58) Field of Classification Search
CPC .. A61K 31/352; A61K 31/658; A61K 9/1617; A61K 9/19; A23L 27/33; A23L 33/105; A23L 27/32; A23V 2002/00
See application file for complete search history.

(56) References Cited

U.S. PATENT DOCUMENTS

| | | | |
|---|---|---|---|
| 6,383,513 B1 | 5/2002 | Watts et al. | |
| 8,530,679 B2 | 9/2013 | Bhatarah et al. | |
| 9,555,019 B2 | 1/2017 | De Vries et al. | |
| 9,616,025 B2 | 4/2017 | De Vries et al. | |
| 10,779,557 B2 | 9/2020 | Franklin et al. | |
| 2009/0298929 A1* | 12/2009 | Jarho | A61P 1/08 514/777 |
| 2016/0143972 A1* | 5/2016 | Stebbins | A61K 36/185 424/725 |
| 2016/0243177 A1 | 8/2016 | Franklin et al. | |

(Continued)

FOREIGN PATENT DOCUMENTS

| | | | | |
|---|---|---|---|---|
| WO | WO-2006051067 A1 * | 5/2006 | ........... | A61K 31/352 |
| WO | 2014030053 A1 | 2/2014 | | |

(Continued)

OTHER PUBLICATIONS

Gorissen et al. (Amino Acids 2018;50:1685-1695) (Year: 2018).*
International Preliminary Report on Patentability in International Application No. PCT/US2021/041992, dated Jan. 26, 2023.
International Search Report and Written Opinion in International Application No. PCT/US2021/041992, dated Dec. 20, 2021.
Drooge et al., "Spray freeze drying to produce a stable Delta9-tetrahydrocannabinol containing inulin-based solid dispersion powder suitable for inhalation", European J. of Pharmaceutical Sciences, 26 (2005) 231-240.

(Continued)

*Primary Examiner* — Ernst V Arnold
(74) *Attorney, Agent, or Firm* — Woodard Emhardt Henry Reeves & Wagner LLP

(57) ABSTRACT

The invention relates to a solid Δ⁹-THC composition containing Δ⁹-THC and a powder former and having a molar ratio of Δ⁹-THC to powder former to form a flowable Δ⁹-THC powder. The powder former is selected from the group consisting of adenine, aspartame, caffeine, lactose, mannitol, nicotinamide, β-nicotinamide adenine dinucleotide, pipecolic acid, saccharin, aspartic acid, glutamic acid, glutamine, histidine, leucine, methionine, phenylalanine, proline, serine, tryptophan, valine, Epigallocatechin Gallate (EGCG), 2-Hydroxypropyl-beta-cyclodextrin (HPbCD), and Trimethyl-beta-cyclodextrin (TOMBC) and mixtures thereof. The invention also relates to methods of making a solid Δ⁹-THC composition of the invention. The Δ⁹-THC may be synthetic Δ⁹-THC or may be extracted Δ⁹-THC. The invention provides pharmaceutical or nutraceutical composition containing a solid Δ⁹-THC composition of the invention and a pharmaceutically- or nutraceutically-acceptable carrier where Δ⁹-THC is present in a pharmaceutically or nutraceutically effective amount. The invention also provides methods of treating a disease, disorder, or condition by administering to a patient in need thereof a therapeutically effective amount of a solid Δ⁹-THC composition. A solid Δ⁹-THC composition of the invention may also be incorporated into food and beverage products.

14 Claims, 21 Drawing Sheets

(56) References Cited

U.S. PATENT DOCUMENTS

| | | | |
|---|---|---|---|
| 2016/0324776 A1* | 11/2016 | Glatzel | A23L 2/52 |
| 2017/0189463 A1* | 7/2017 | Franklin | A61K 38/02 |
| 2018/0098552 A1* | 4/2018 | Bhairam | A23F 5/14 |
| 2018/0271826 A1* | 9/2018 | Sievers | A61K 9/146 |
| 2018/0369191 A1* | 12/2018 | Muscarella | A61P 19/02 |
| 2019/0041321 A1 | 2/2019 | Linden | |
| 2019/0254326 A1* | 8/2019 | Welsh | A23P 10/40 |
| 2020/0197356 A1* | 6/2020 | Firger | A61K 31/352 |
| 2020/0253922 A1 | 8/2020 | Boylan et al. | |
| 2020/0315103 A1 | 10/2020 | Leo | |
| 2021/0401736 A1 | 12/2021 | Wan et al. | |
| 2022/0016072 A1 | 1/2022 | Rigsbee et al. | |

FOREIGN PATENT DOCUMENTS

| | | |
|---|---|---|
| WO | 2017183011 A1 | 10/2017 |
| WO | 2019211772 A1 | 11/2019 |
| WO | 2020072997 A1 | 4/2020 |
| WO | 2021102353 A1 | 5/2021 |

OTHER PUBLICATIONS

Zagzoog, Ayat et al., Modulation of type 1 cannabinoid receptor activity by cannabinoid by-products from Cannabis sativa and non-cannabis phytomolecules. Frontiers in Parmacology, Aug. 26, 2022. 13 pages.

Nelson, Nnamdi G. et al., Joint and separate exposure to alcohol and Δ9-tetrahydrocannabinol produced distinct effects on glucose and insulin homeostasis in male rats. Nature Research, Scientific Reports, Aug. 19, 2019. 12 pages.

* cited by examiner

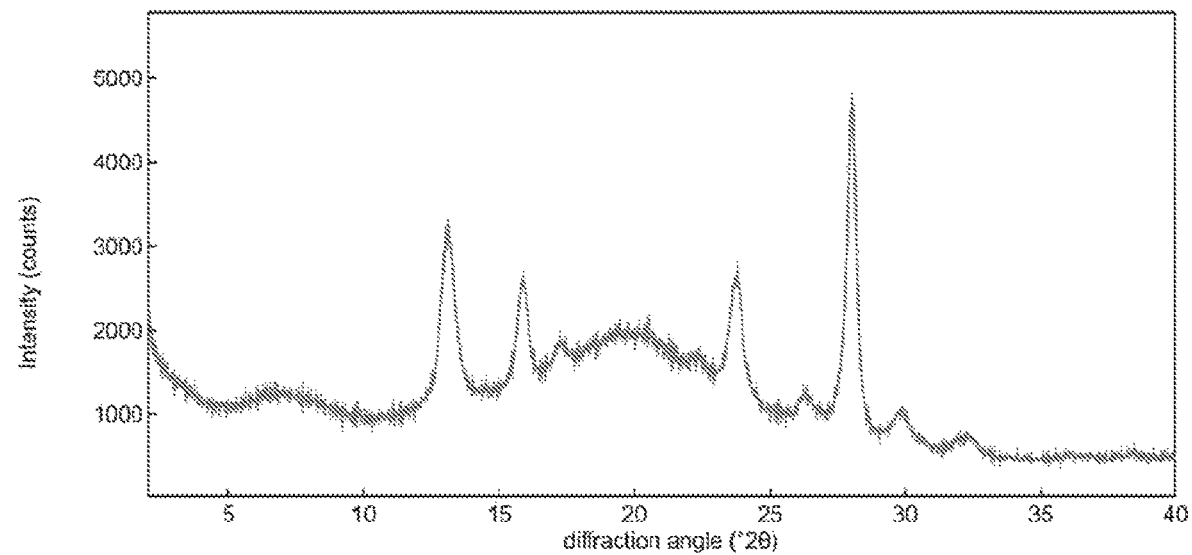
FIG. 1: Freeze-dried 1:1 THC/Adenine Powder
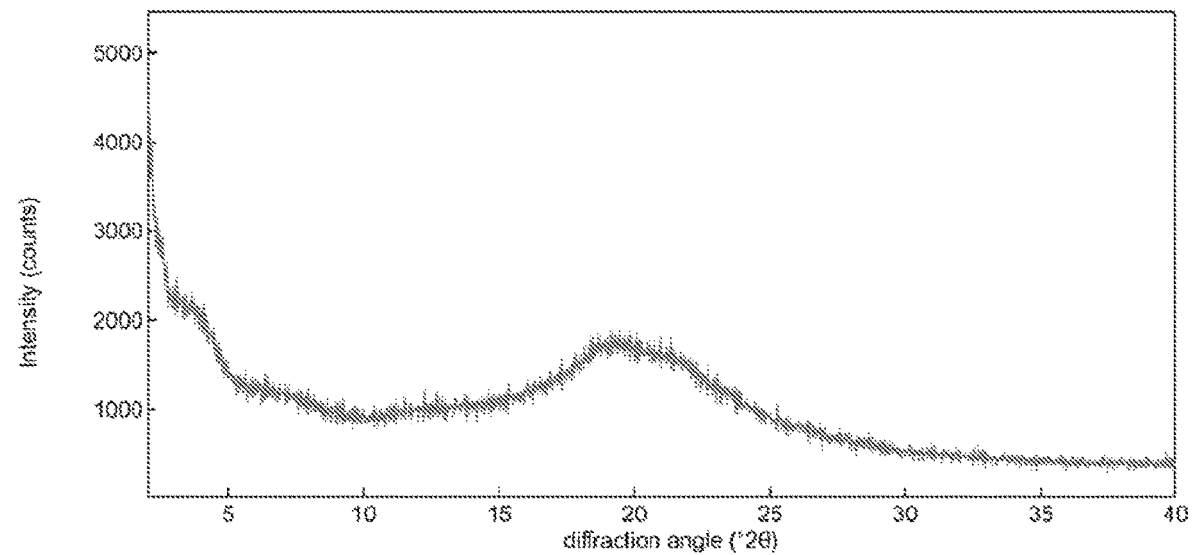
FIG. 2 Freeze-dried 1:1 THC/Aspartame Powder

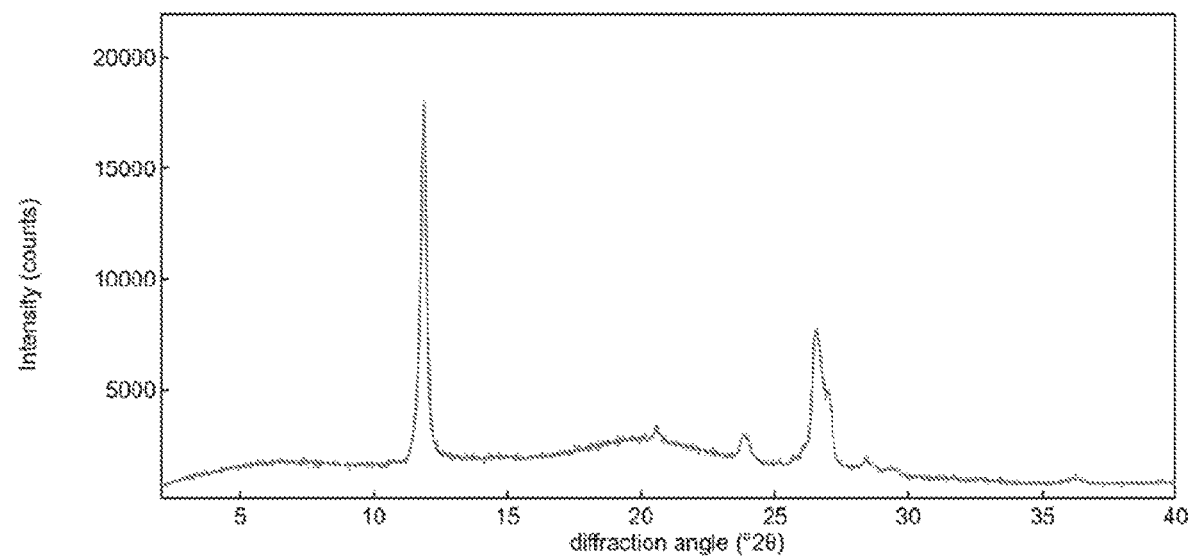
FIG. 3: Freeze-dried 1:1 THC/Caffeine Powder
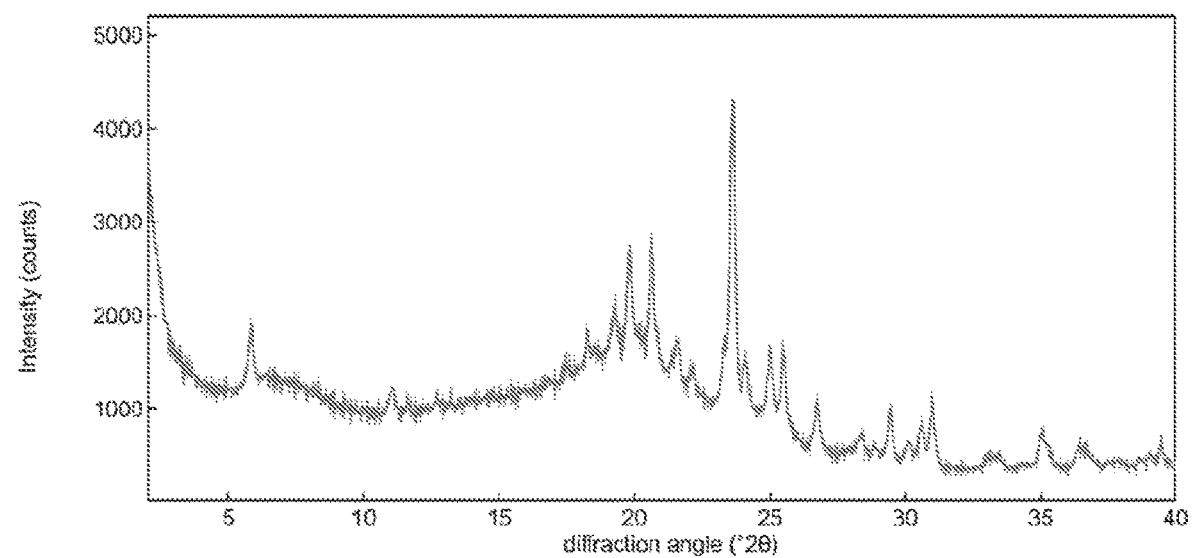
FIG. 4: Freeze-dried 1:1 THC/Glutamine Powder FIG. 5: Freeze-dried 1:1 THC/Histidine Powder
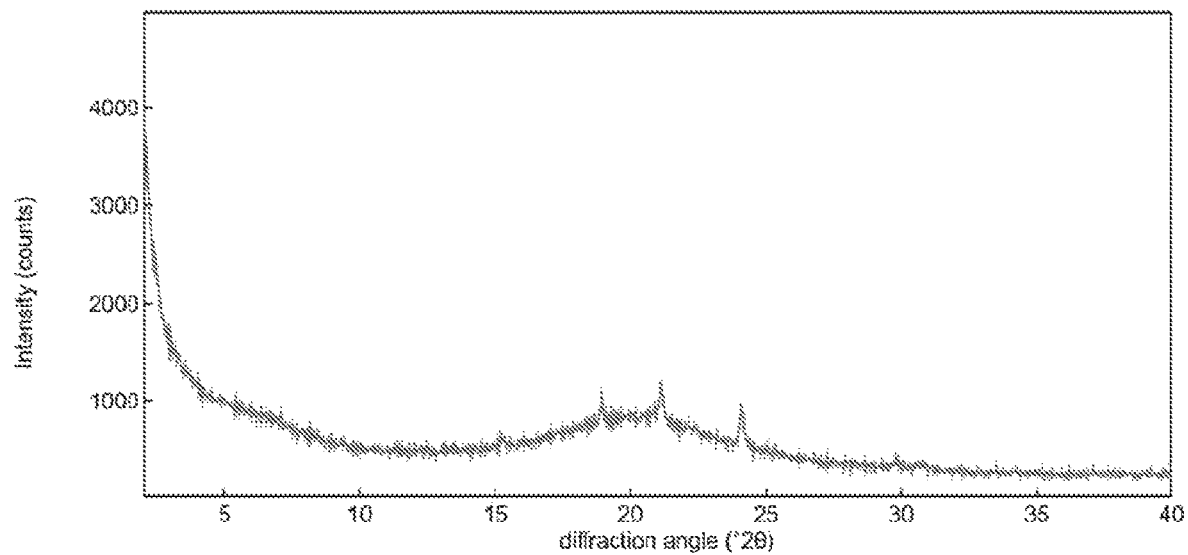
FIG. 6: Freeze-dried 1:1 THC/Lactose Powder
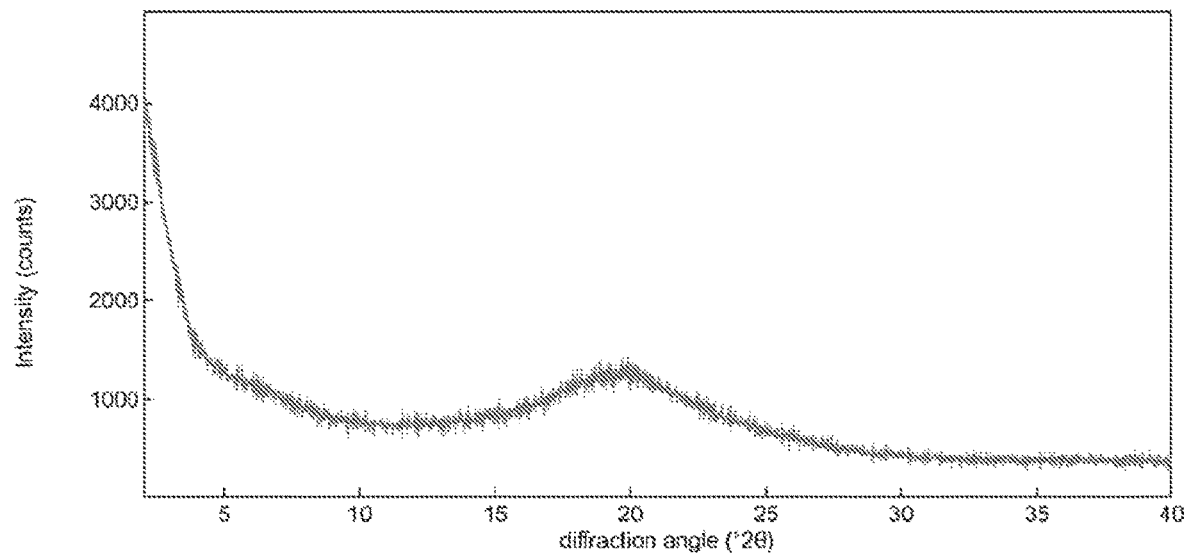

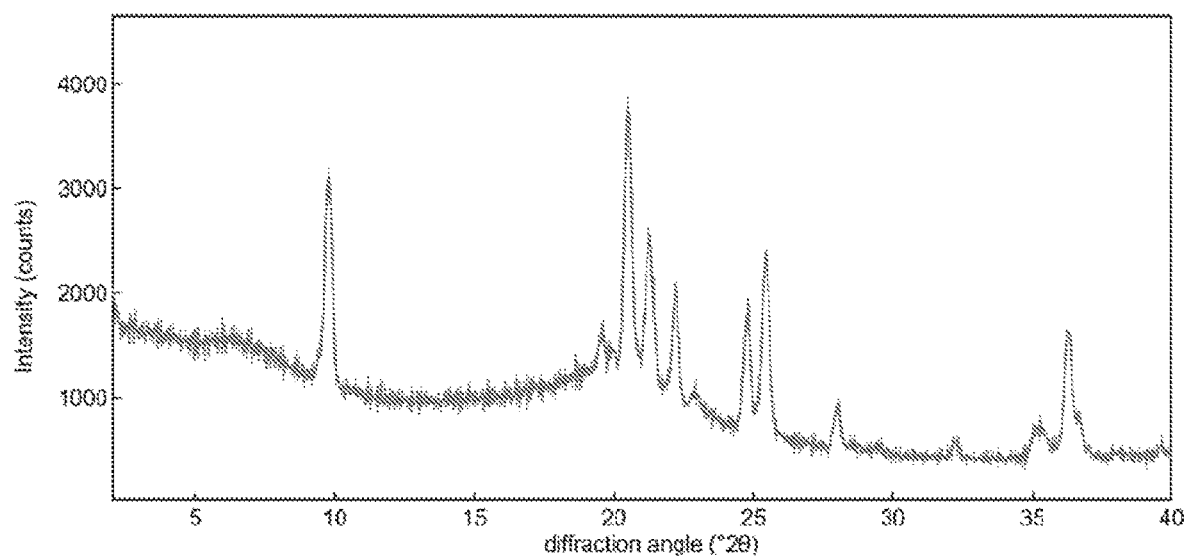
FIG. 7: Freeze-dried 1:1 THC/D-Mannitol Powder
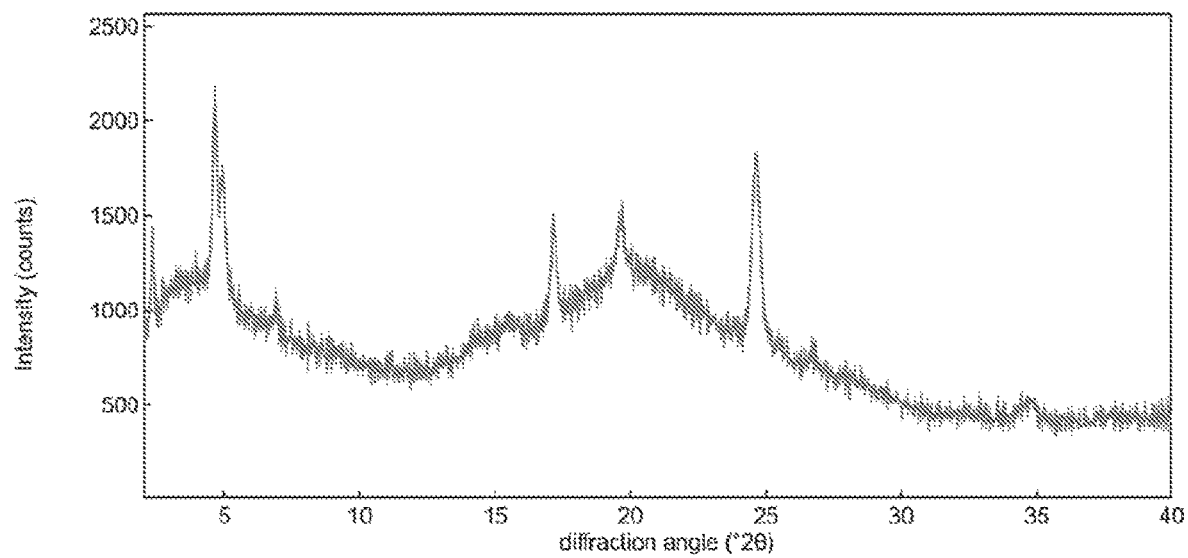
FIG. 8: Freeze-dried 1:1 THC/Nicotinamide Powder FIG. 9: Freeze-dried 1:1 THC/L-Pipecolic Acid Powder
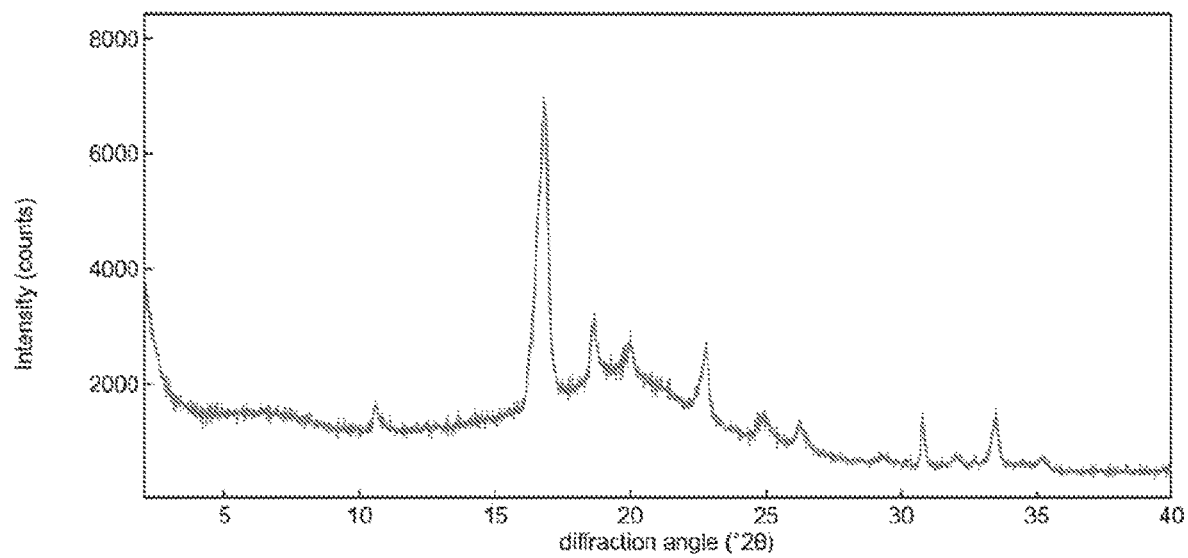
FIG. 10: Freeze-dried 1:1 THC/Saccharin Powder
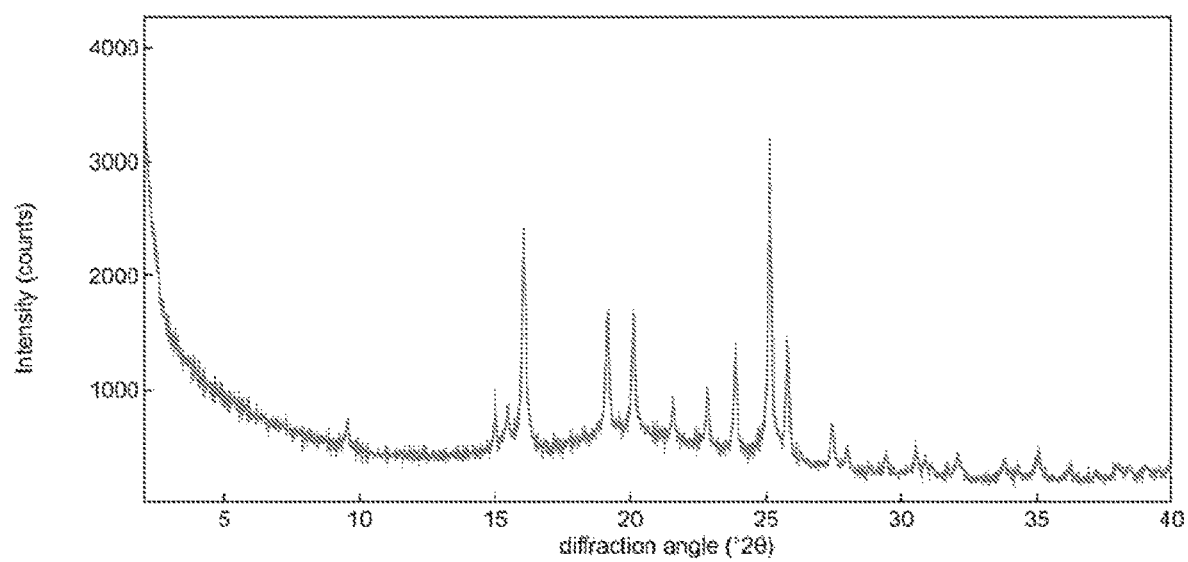

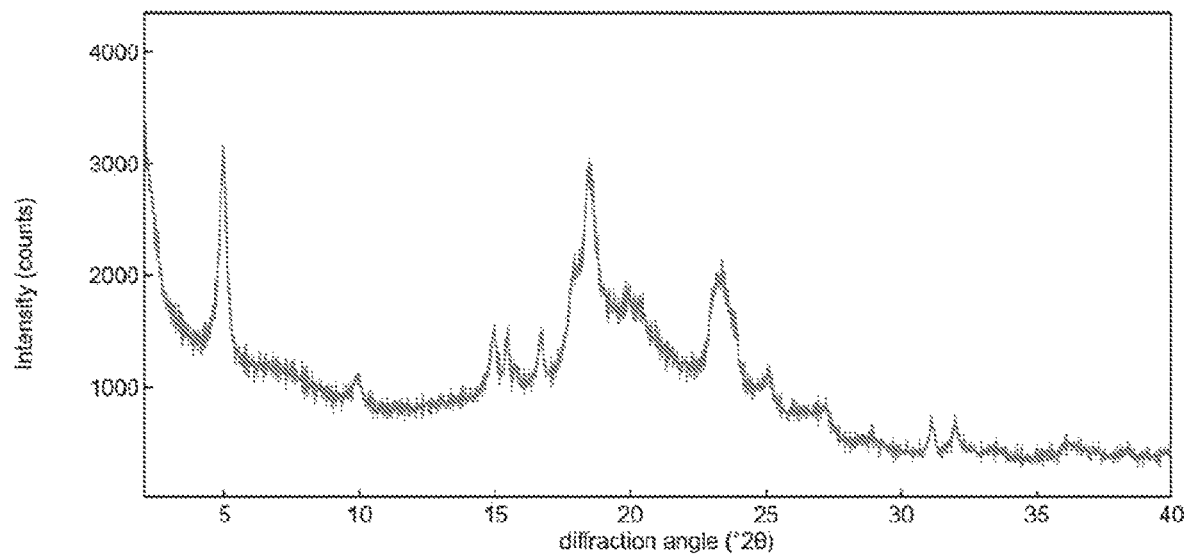
FIG. 11: Freeze-dried 1:1 THC/L-Tryptophan Powder
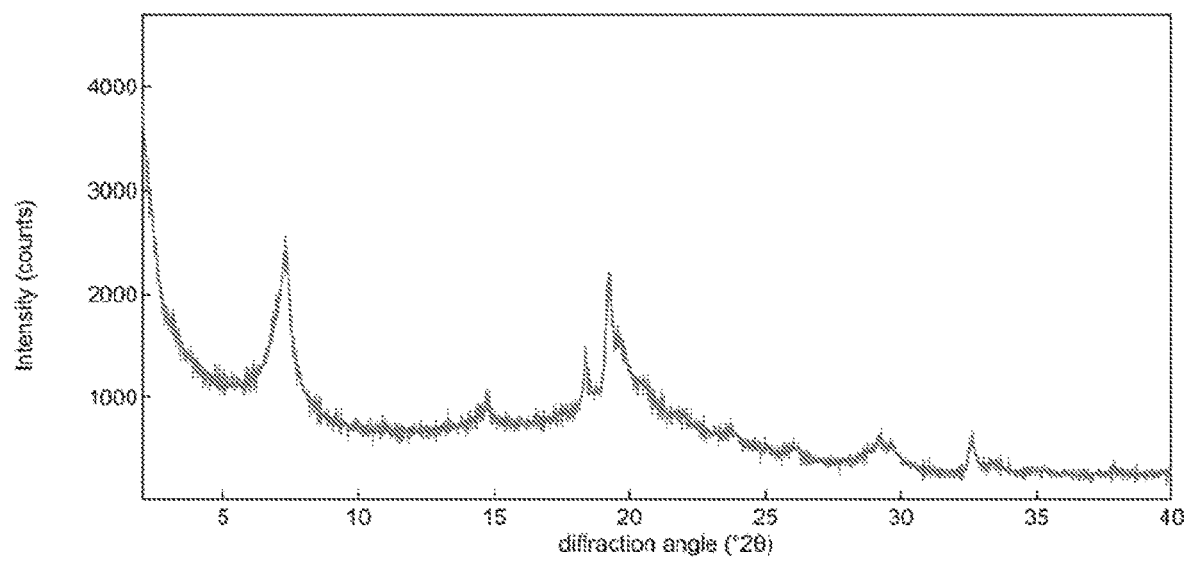
FIG. 12: Freeze-dried 1:1 THC/L-Valine Powder FIG. 13: Freeze-dried 1:4 THC/L-Aspartic Acid Powder
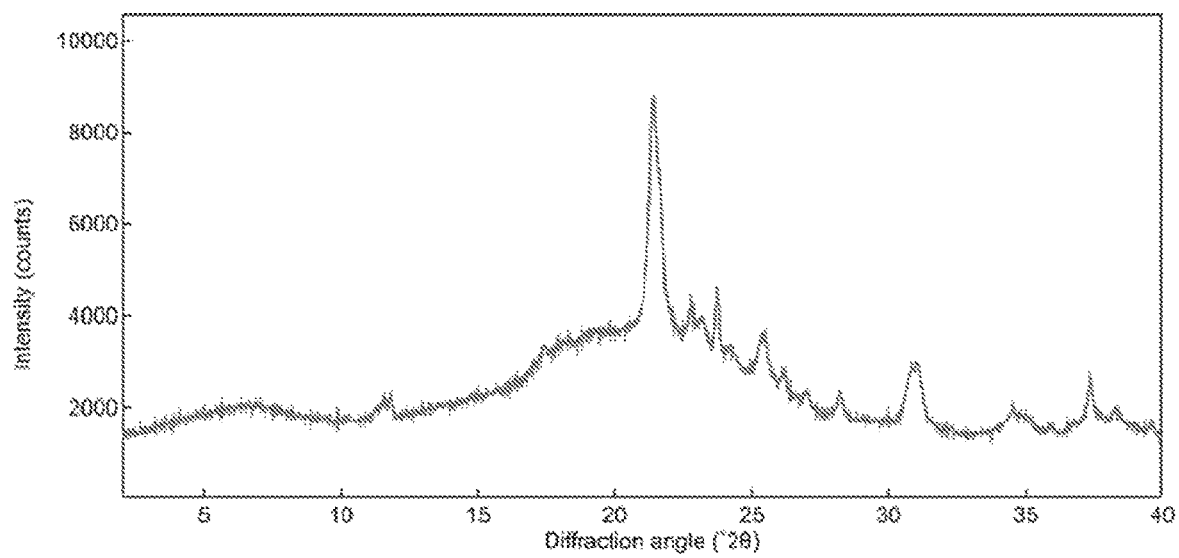
FIG. 14: Freeze-dried 1:4 THC/L-Glutamic Acid Powder
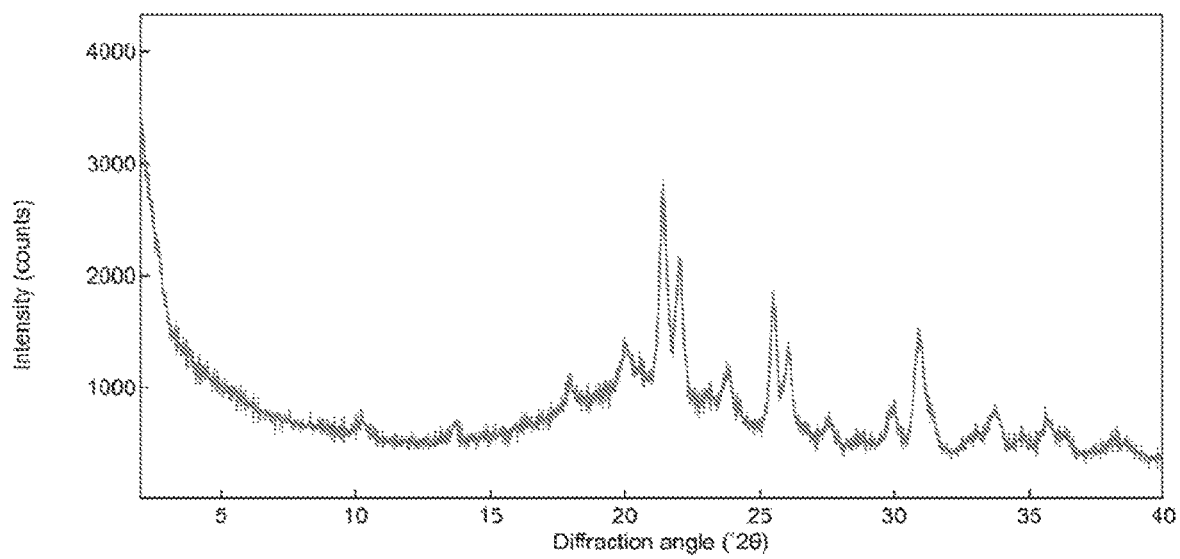

FIG. 15: Freeze-dried 1:4 THC/L-Leucine Powder
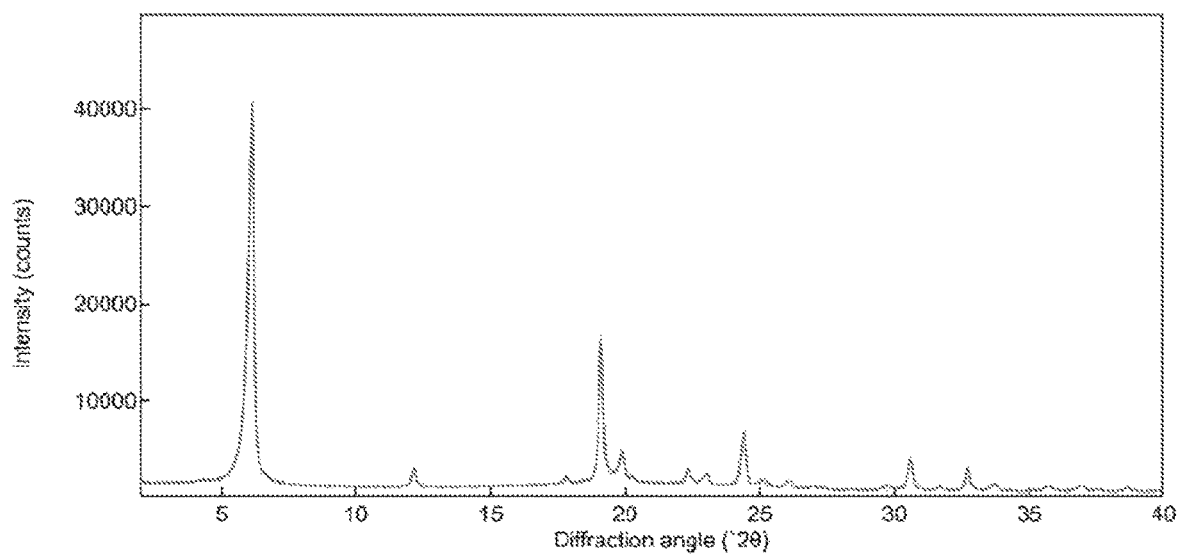
FIG. 16: Freeze-dried 1:4 THC/L-Methionine Powder
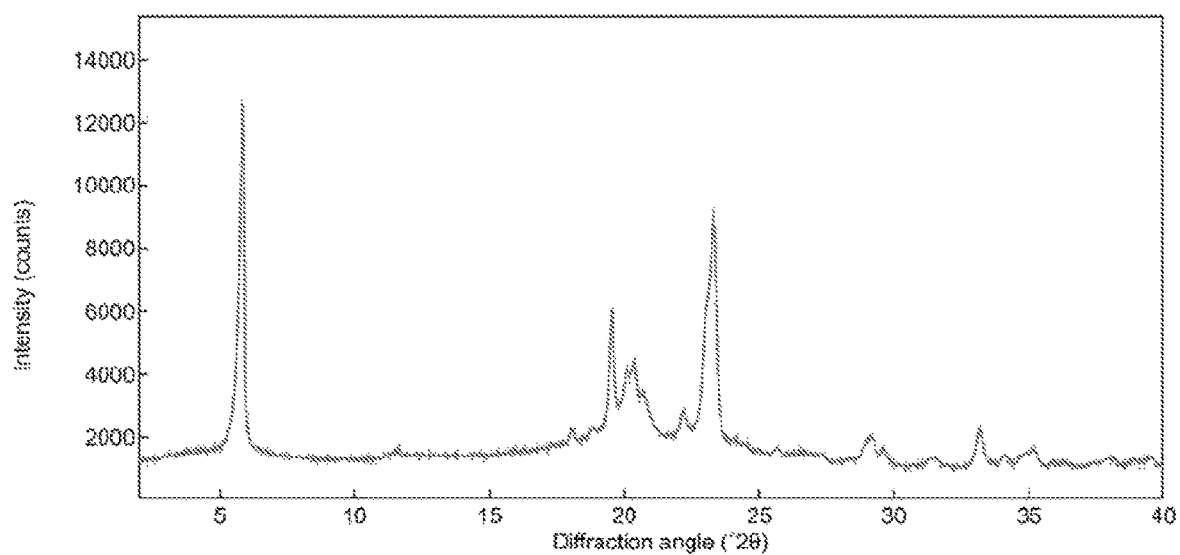

FIG. 17: Freeze-dried 1:4 THC/β-nicotinamide Adenine Dinucleotide Powder
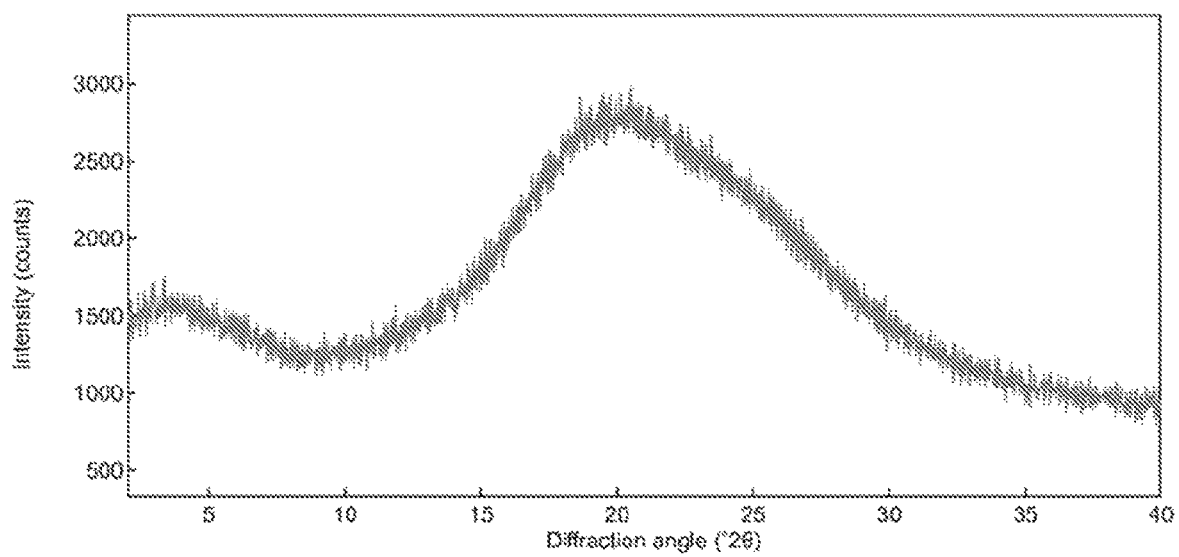
FIG. 18: Freeze-dried 1:2 THC/L-Phenylalanine Powder
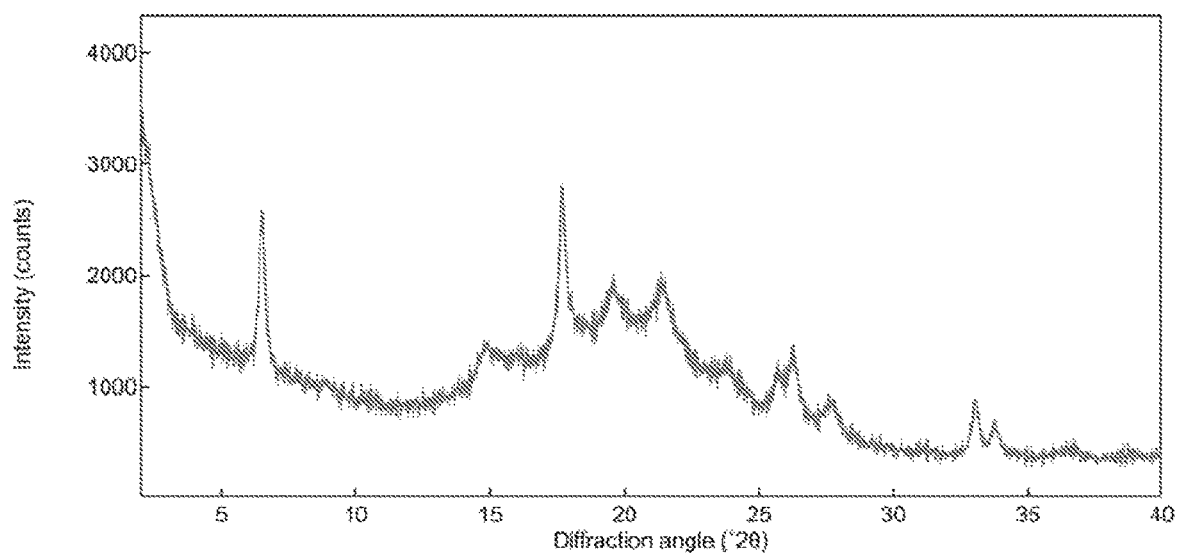

FIG. 19: Freeze-dried 1:4 THC/L-Proline Powder
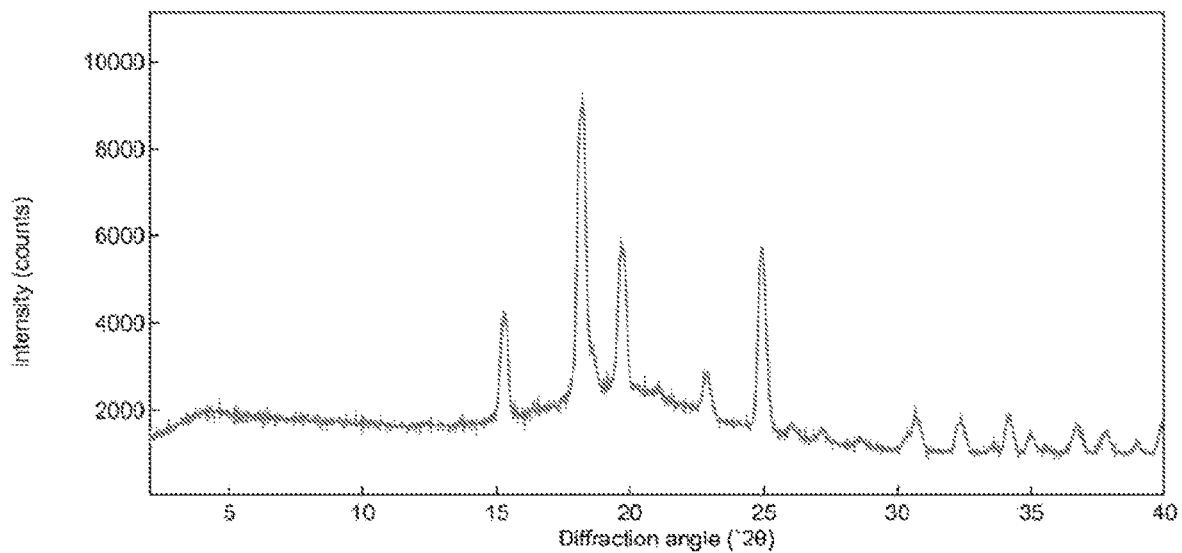
FIG. 20: Freeze-dried 1:4 THC/L-Serine Powder
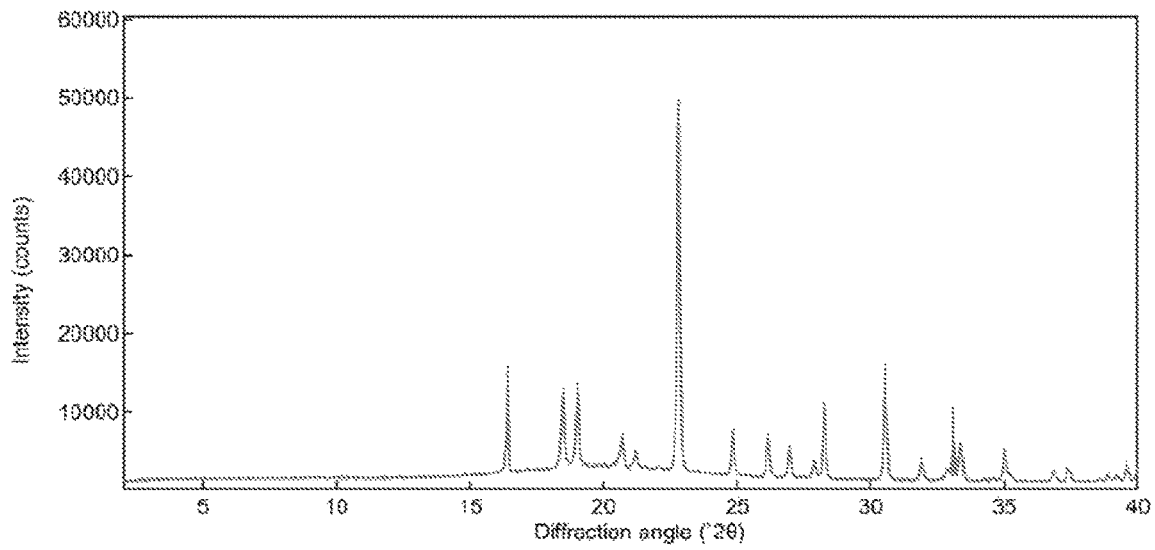

FIG. 21: THC/Aspartame 1:1 Powder by Evaporation
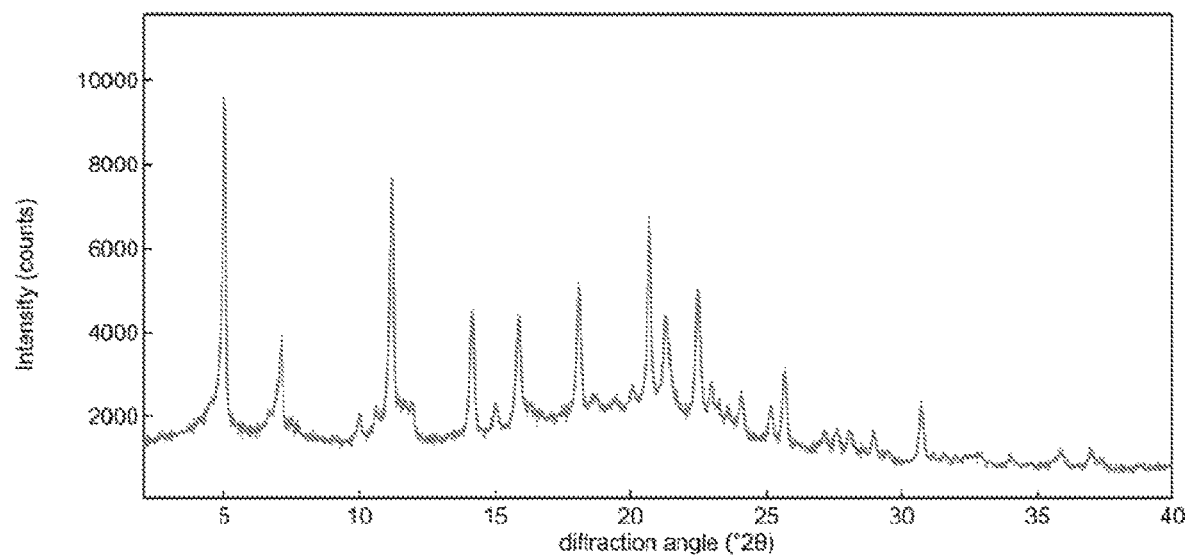
FIG. 22: THC/Caffeine 1:1 Powder by Evaporation
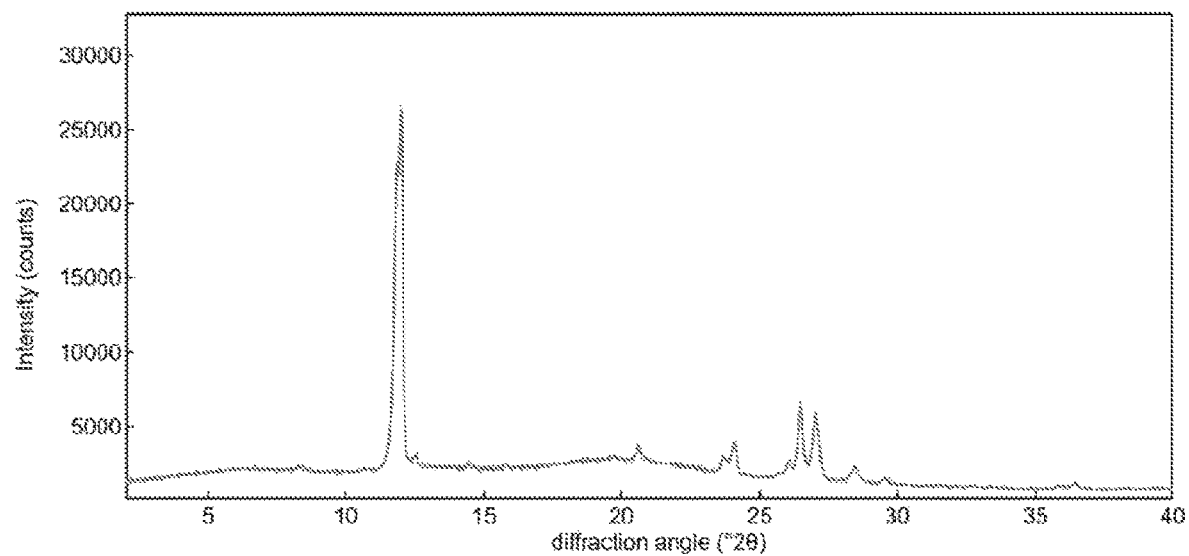

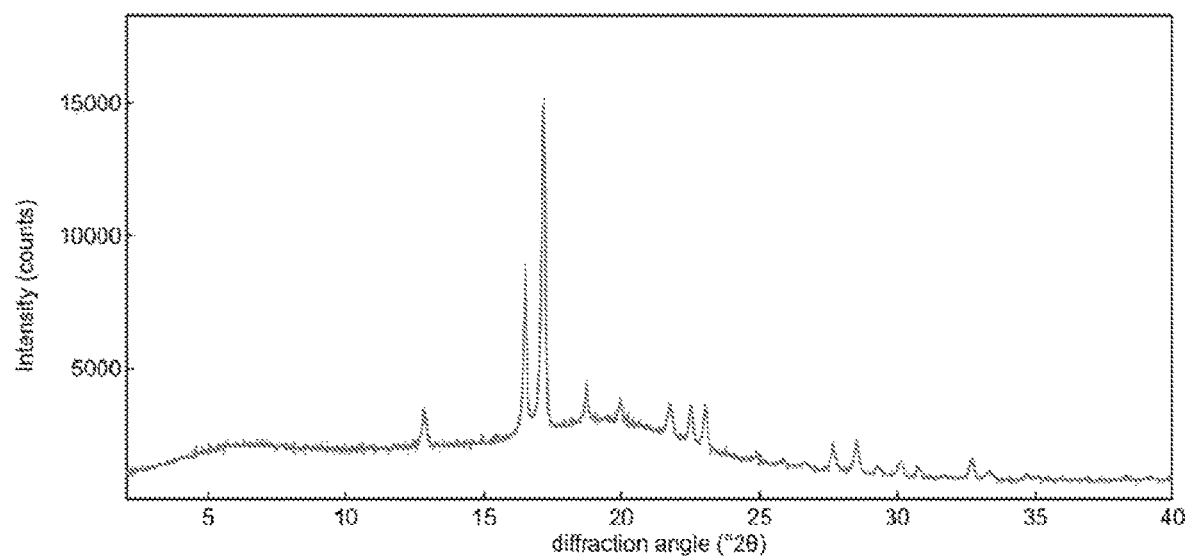
FIG. 23: THC/L-Pipecolic Acid 1:1 Powder by Evaporation
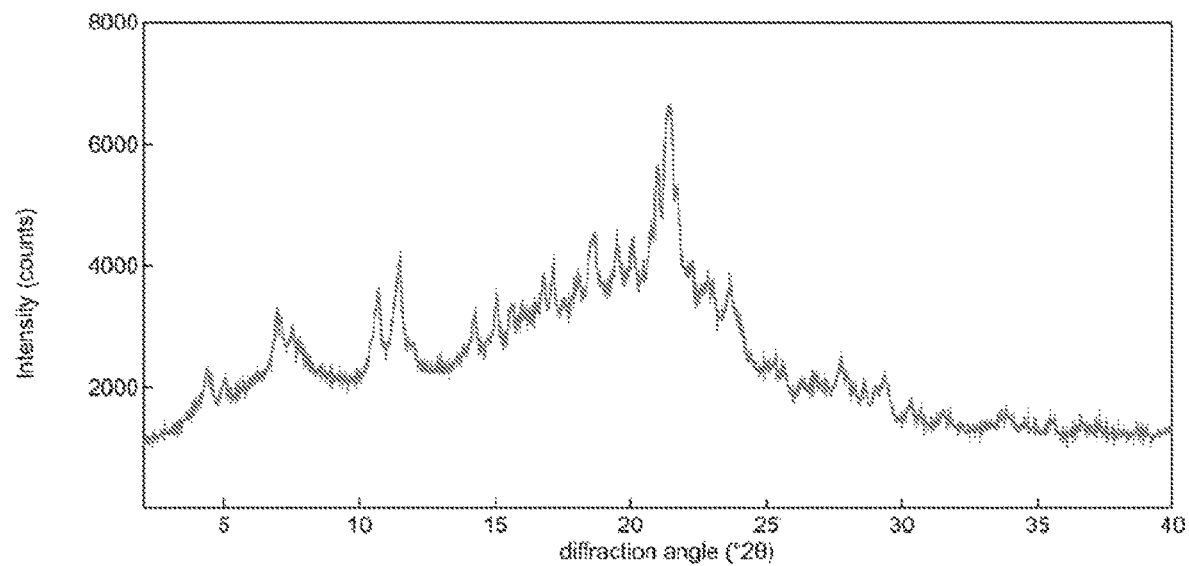
FIG. 24: THC/Aspartame 1:1 Powder by Physical Mixing FIG. 25: THC/Caffeine 1:1 Powder by Physical Mixing
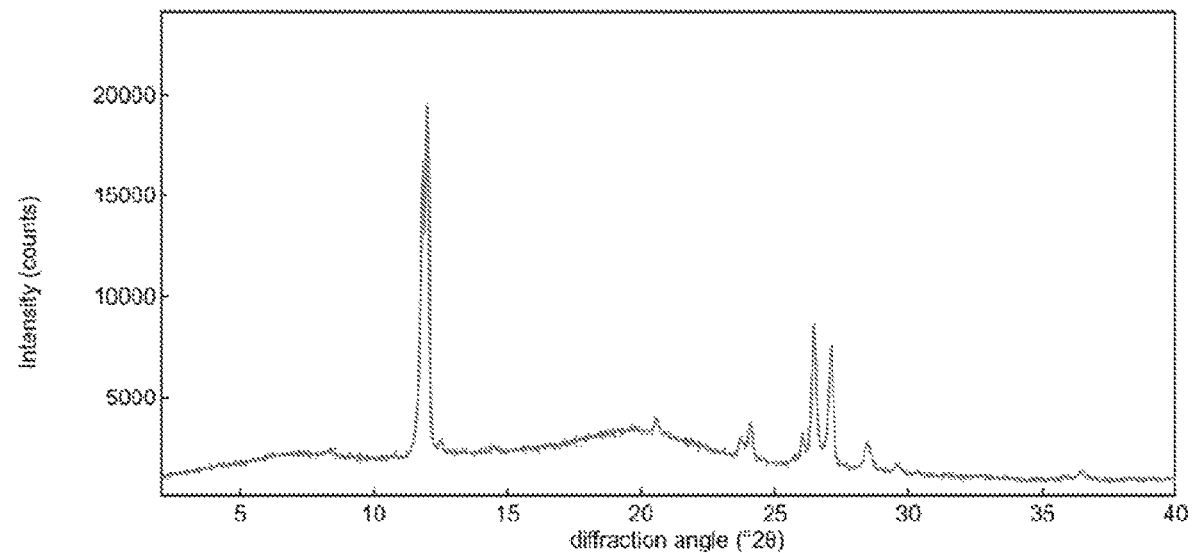
FIG. 26: THC/Lactose 1:1 Powder by Physical Mixing
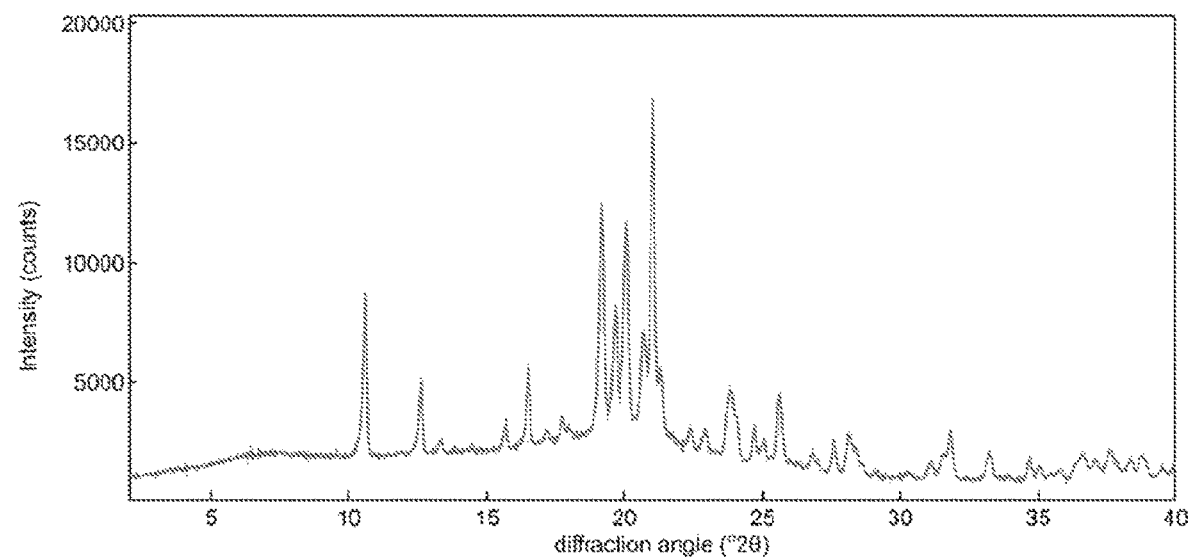

FIG. 27: THC/L-Pipecolic Acid 1:1 Powder by Physical Mixing
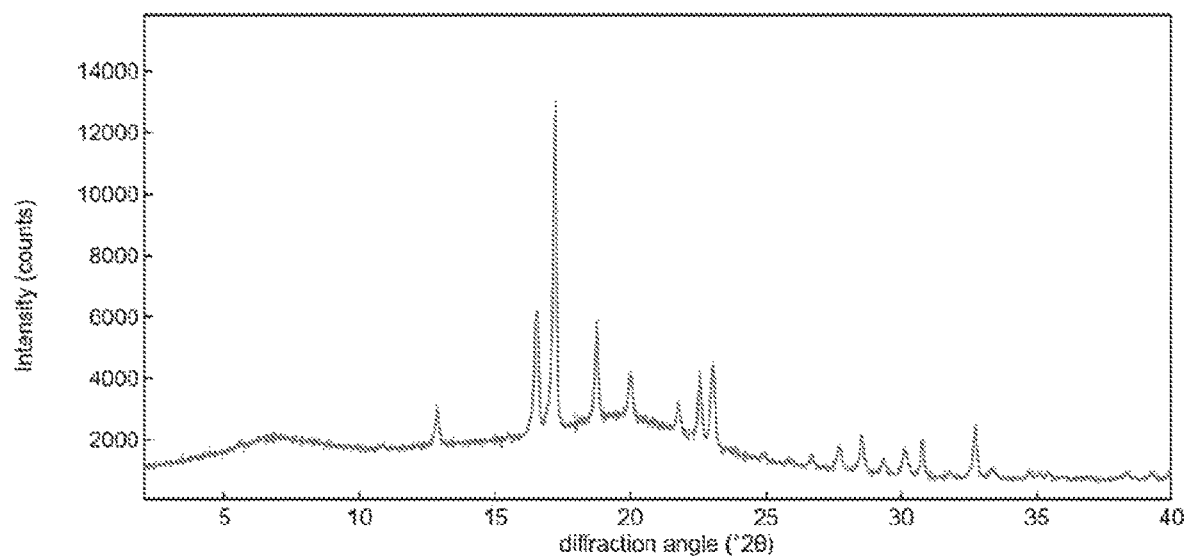
FIG. 28: Freeze-dried 2:1 THC/EGCG Powder
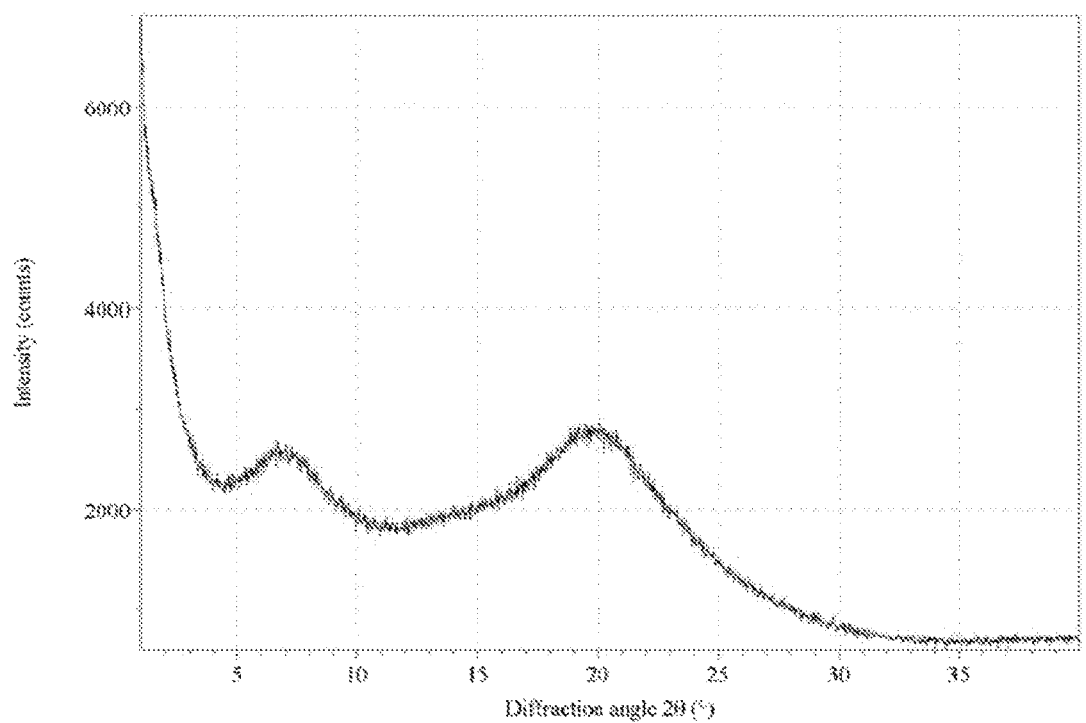

FIG. 29: Freeze-dried 1:2 THC/L-glutamine Powder
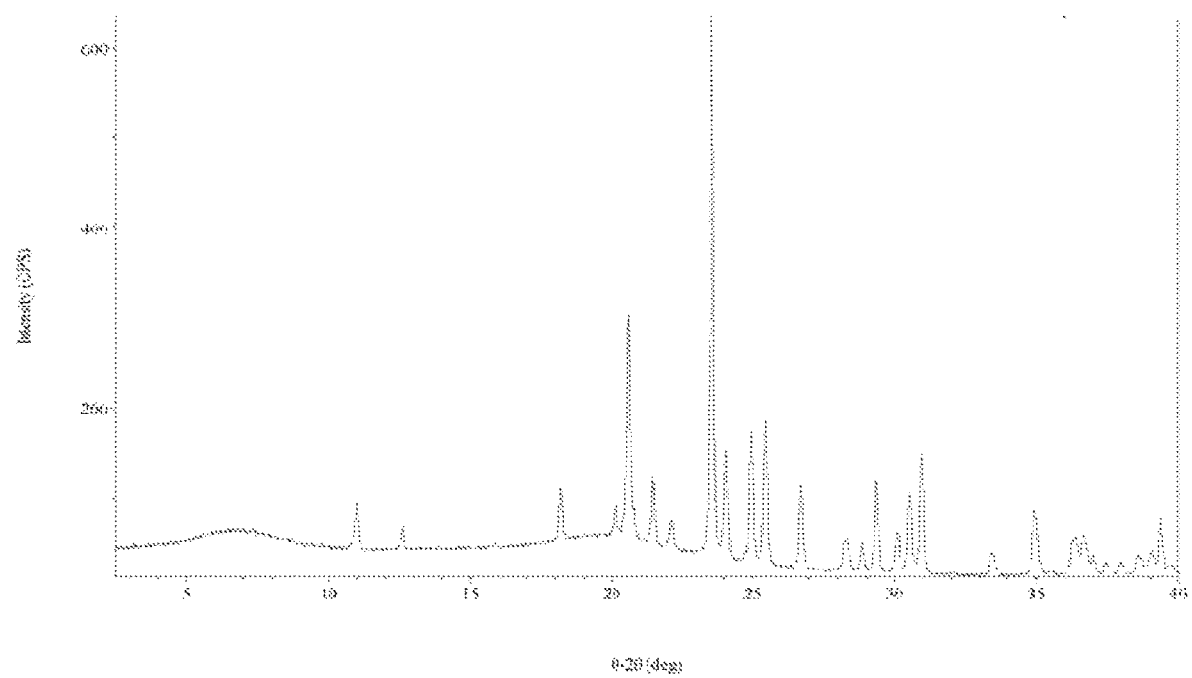
FIG. 30: THC/HPbCD 1:1 Powder by Rotary Evaporation
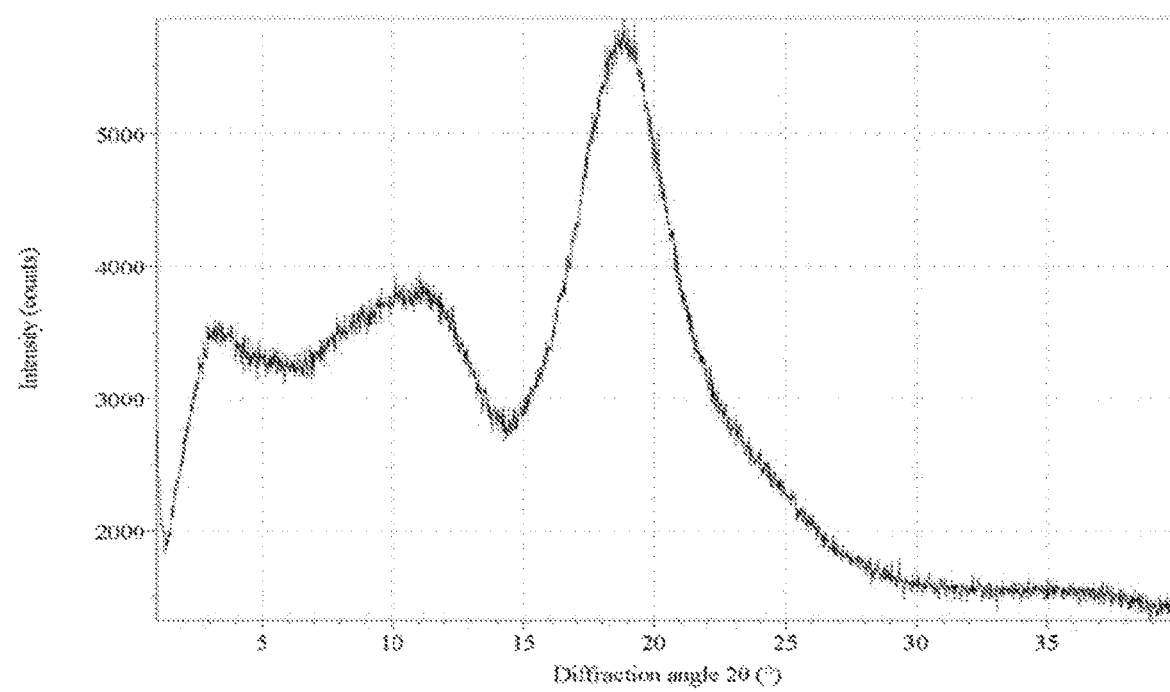

FIG. 31: THC/TOMBC 1:1 Powder by Rotary Evaporation
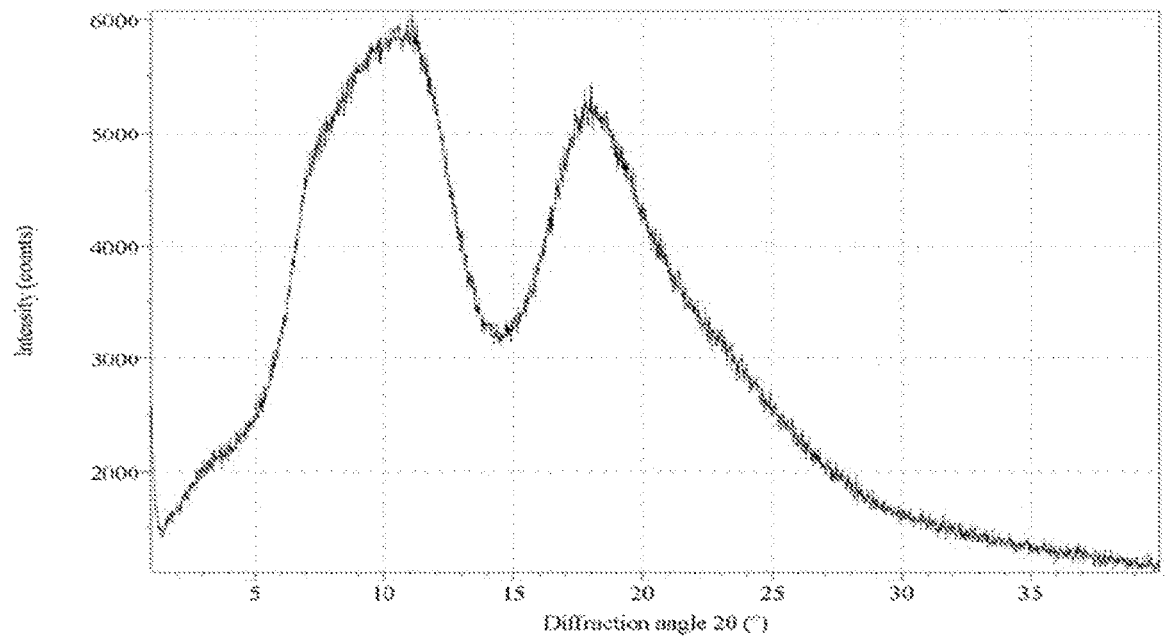
FIG. 32: Freeze-dried 1:2 THC/Aspartame Powder
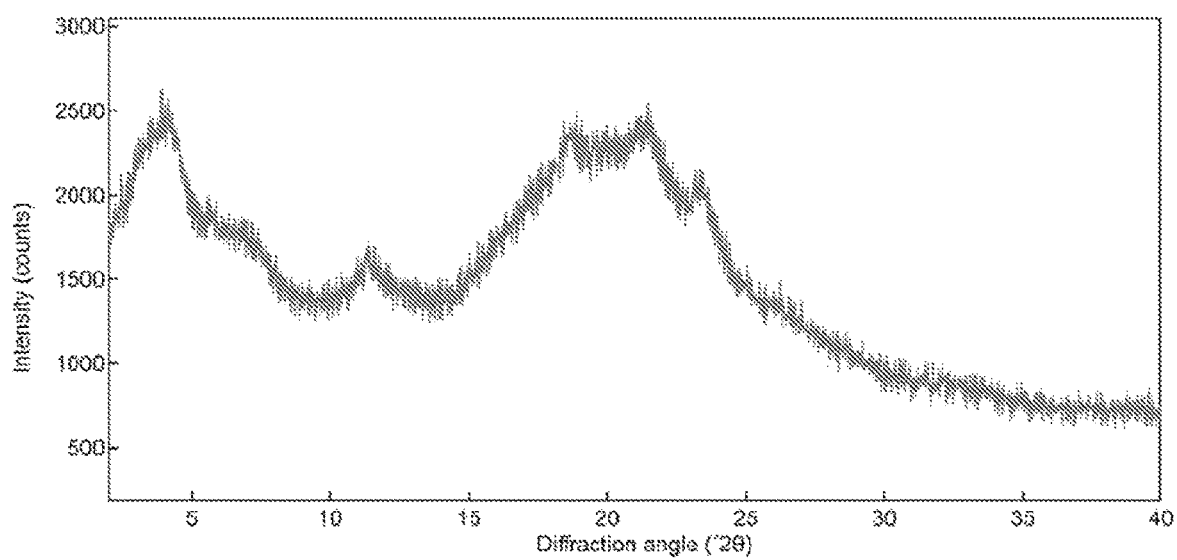

FIG. 33: Freeze-dried 1:4 THC/Aspartame Powder
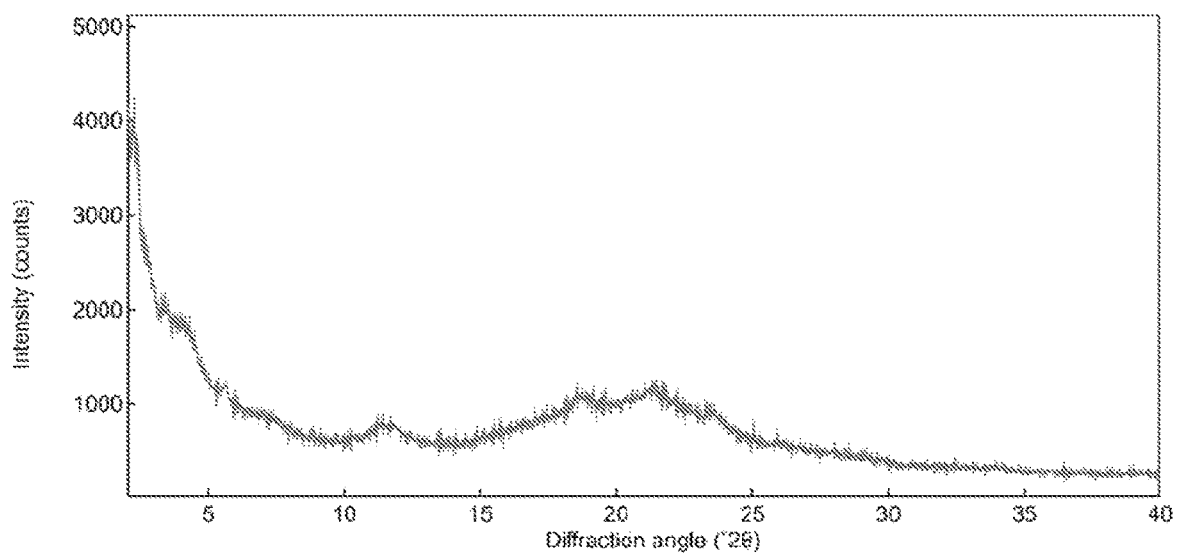
FIG. 34: Freeze-dried 2:1 THC/Aspartame Powder
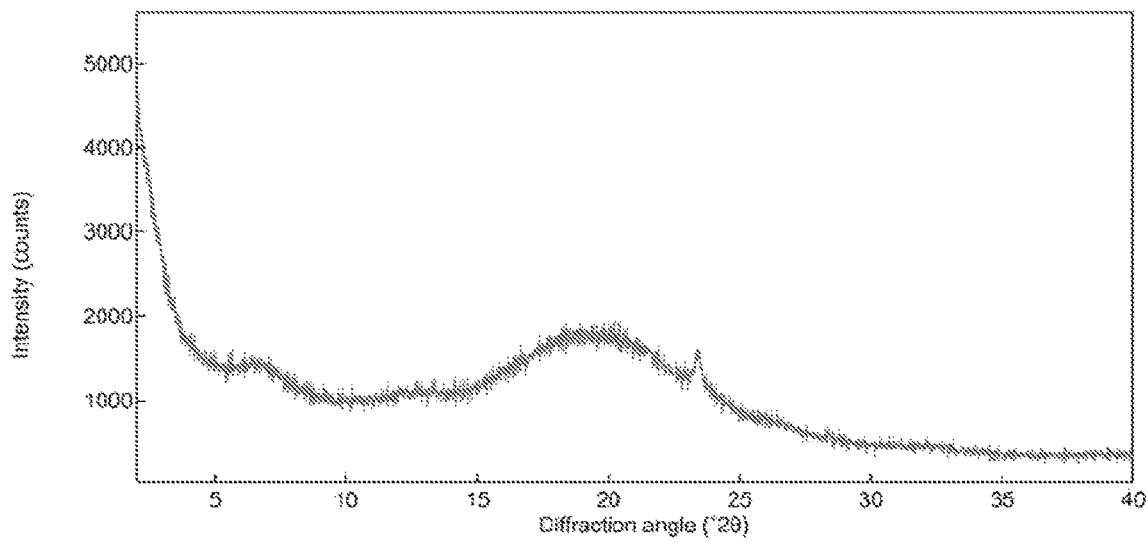

FIG. 35: Freeze-dried 4:1 THC/Aspartame Powder
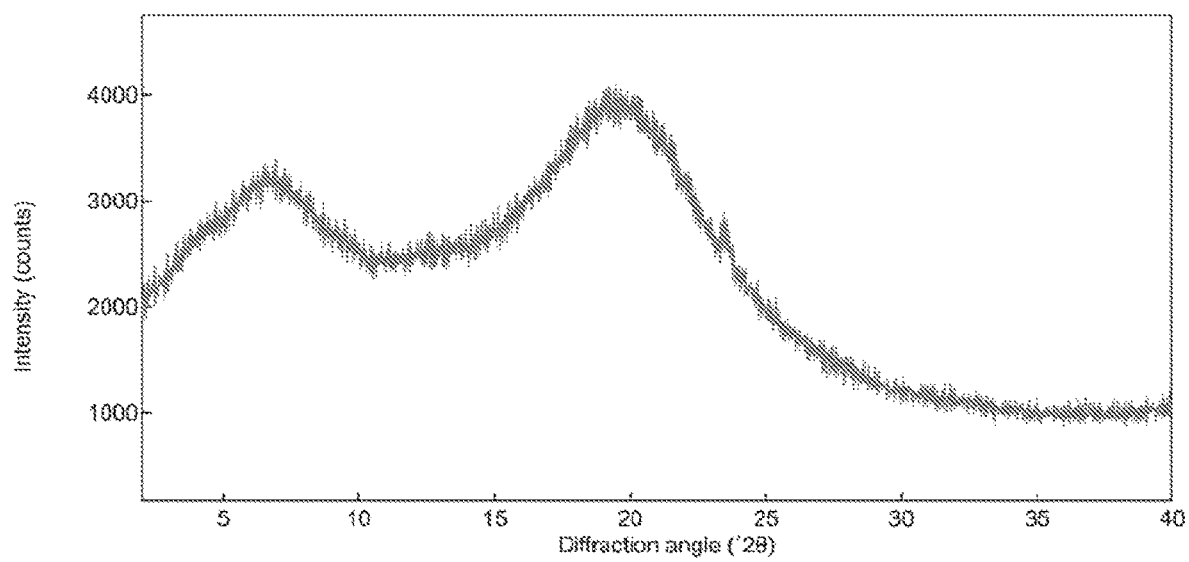
FIG. 36: Freeze-dried 1:2 THC/L-Valine Powder
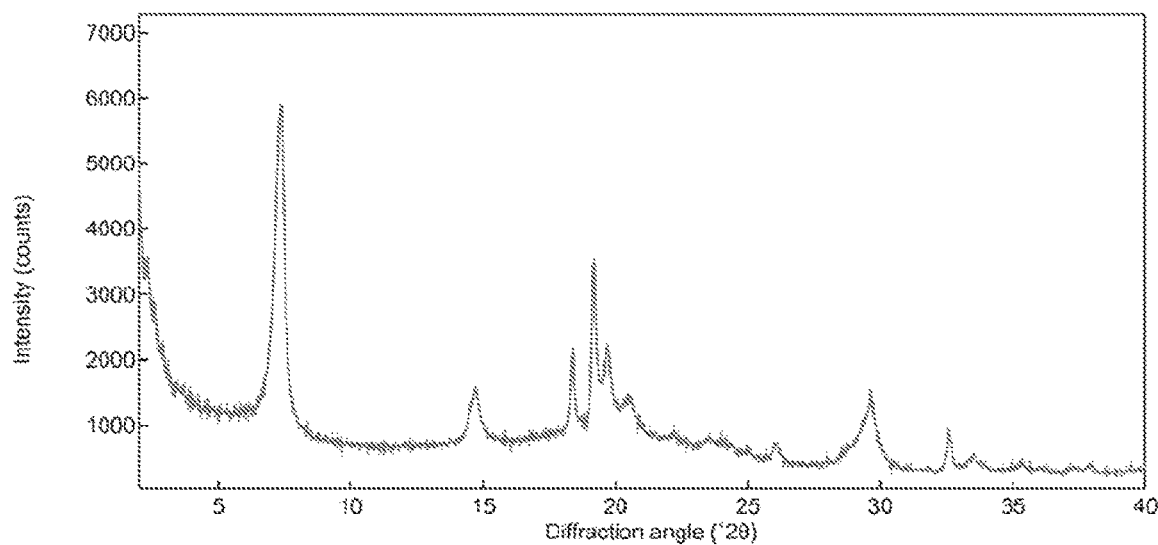

FIG. 37: Freeze-dried 1:4 THC/L-Valine Powder
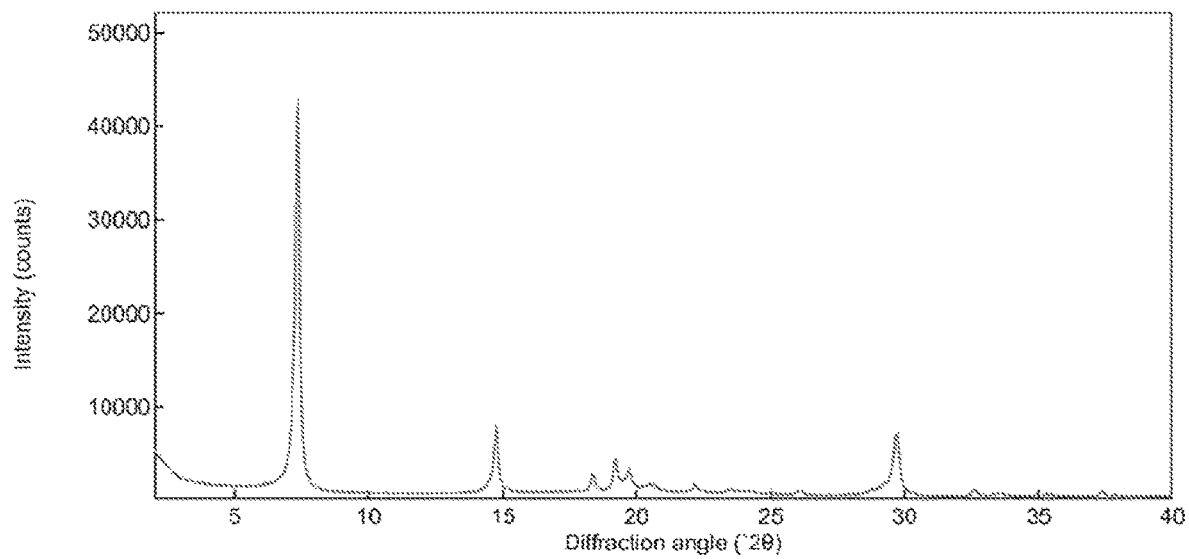
FIG. 38: Freeze-dried 2:1 THC/L-Valine Powder
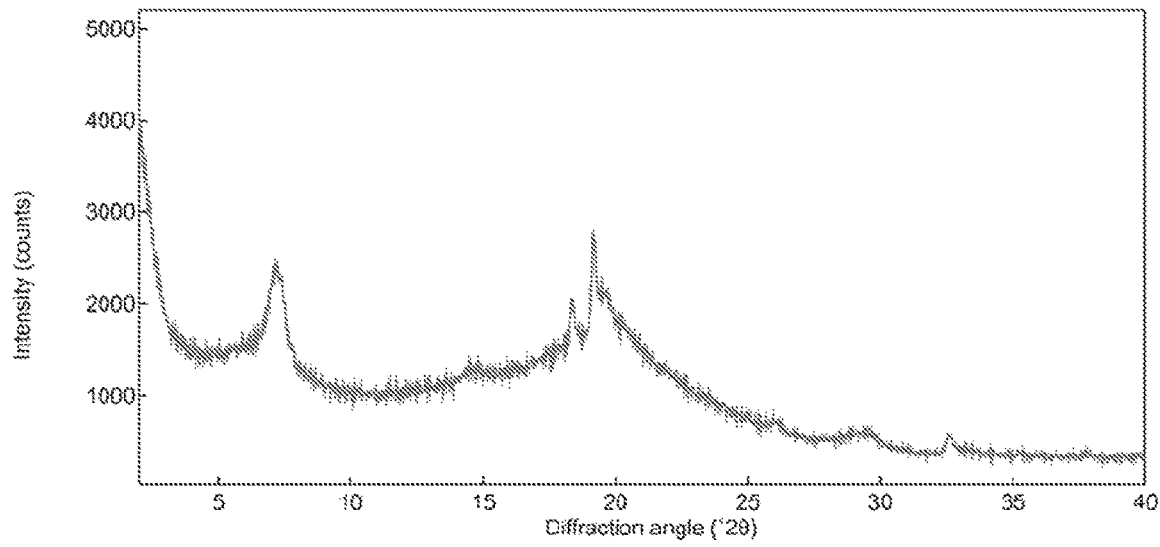

FIG. 39: Freeze-dried 4:1 THC/L-Valine Powder
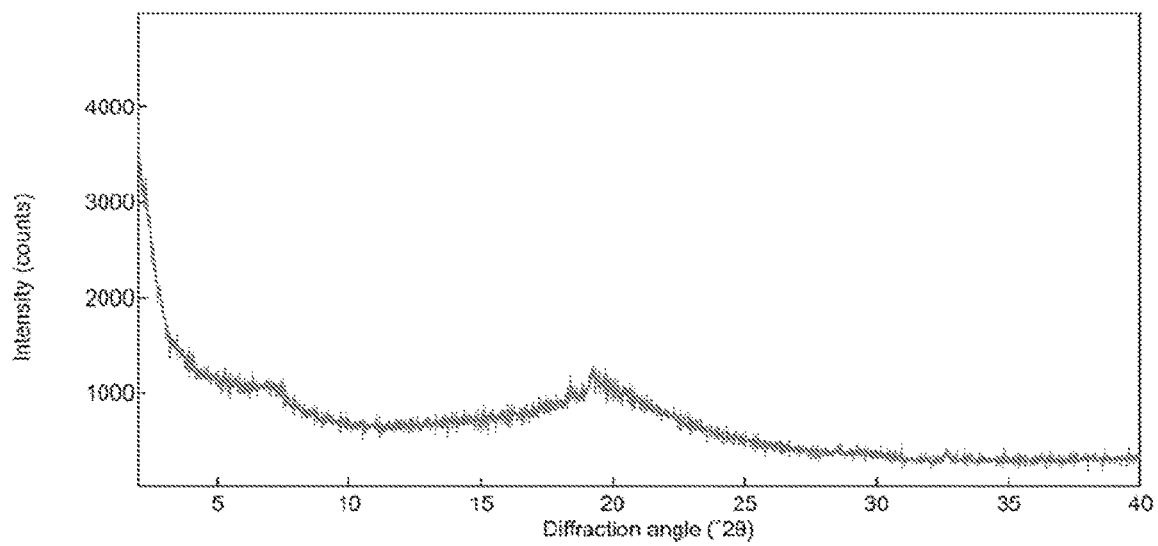
FIG. 40: Freeze-dried 1:2 THC/Caffeine Powder
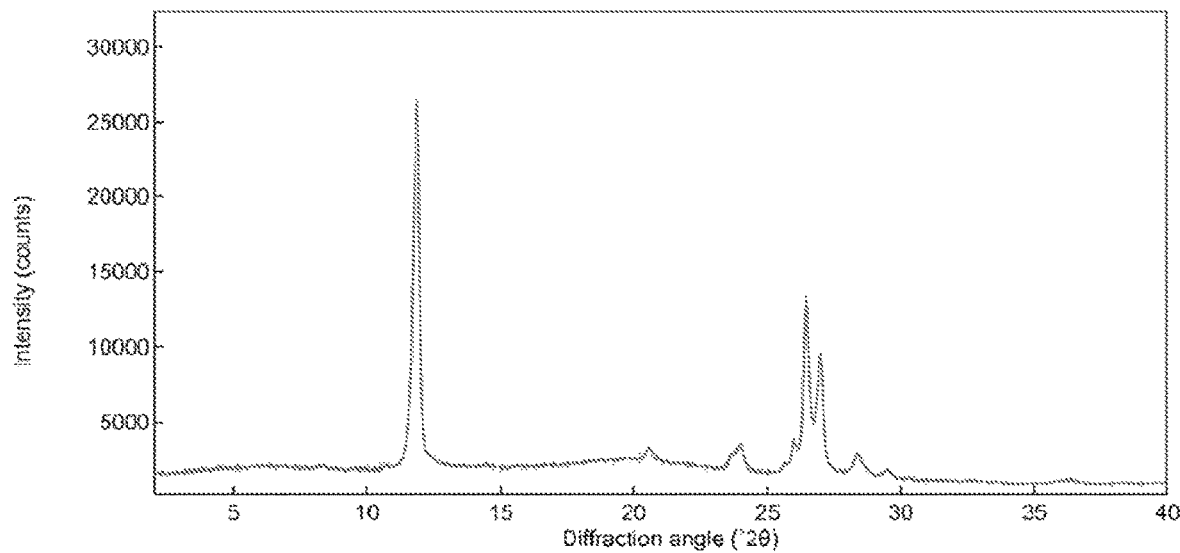

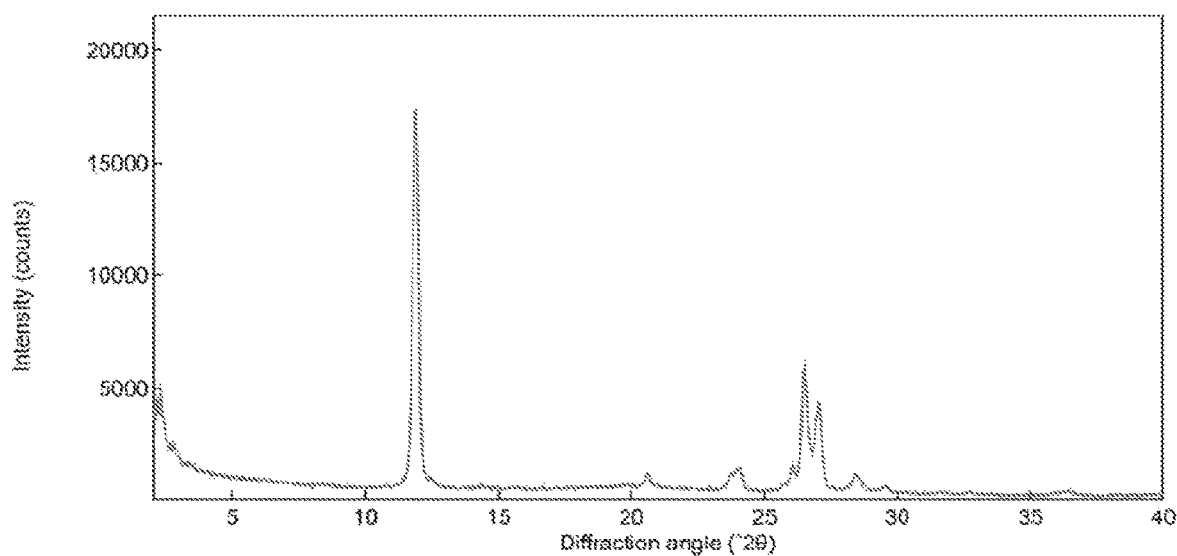
FIG. 41: Freeze-dried 1:4 THC/Caffeine Powder

SOLID Δ⁹-TETRAHYDROCANNABINOL (Δ⁹-THC) COMPOSITIONS

CROSS-REFERENCE TO RELATED APPLICATIONS

This application is a Continuation Application of U.S. application Ser. No. 17/575,035, filed on Jan. 13, 2022; which is a Continuation Application of PCT International Application No. PCT/US2021/041992, filed on Jul. 16, 2021; which claims priority to U.S. patent application 63/053,205, filed Jul. 17, 2020; to U.S. patent application 63/154,151, filed Feb. 26, 2021; and to U.S. patent application 63/154,153, filed Feb. 26, 2021. The disclosure of each application is incorporated herein by reference.

BACKGROUND

*Cannabis* has been a traditional drug and remedy in many cultures and for a long time. *Cannabis* was used for the treatment of various disorders—ranging from asthma to migraine—until the early 20th century. For an overview of natural cannabinoid compounds see David T. Brown ed., *Cannabis*, Hardwood Academic Publishers 1998, ISBN 90-5702-291-5. Tetrahydrocannabinol (THC), more specifically (−)-trans-Δ⁹-tetrahydrocannabinol (Δ⁹-THC) and its isomers, is the psychoactive component in *cannabis*. Recently, though it is a controlled substance, Δ⁹-THC has found therapeutic use as an appetite stimulant and an anti-emetic. An example of a marketed Δ⁹-THC product is Marinol® (generic name dronabinol). Currently, the Δ⁹-THC product is formulated as a soft gelatin capsule for oral administration in which the drug is dissolved in an oil. The disadvantage is that in this formulation Δ⁹-THC is not stable. Consequently, it has to be stored at low temperatures (4° C.). Δ⁹-THC is chemically unstable to light, oxygen and heat. The low stability of a compound and the need to store the pharmaceutical formulation in the refrigerator is a serious drawback for a pharmaceutical product. Therefore, there is a need for stable formulations of Δ⁹-THC, which can be stored, for example, at ambient conditions for prolonged times.

Furthermore, purified Δ⁹-THC is a thick, brown, viscous, resinous material that has been compared to pine-tree sap and/or rubber cement. Accordingly, Δ⁹-THC is extremely difficult to formulate and is not readily adapted for incorporation into standard dosage forms that are typically available for other, solid pharmaceutical compounds. In light of the difficulties associated with its formulation, it would be desirable to have a method to obtain such a drug substance in a solid, powder state.

Accordingly, there is also a need to have Δ⁹-THC formulations that contain specific, known amounts of Δ⁹-THC and which may be used to prepare pharmaceutical compositions of Δ⁹-THC for therapeutic use. Flowable powders offer the possibility to develop other dosage forms, for example, dry powder formulations for pulmonary delivery and tablets for oral or sublingual administration. There is a need for solid Δ⁹-THC compositions. This invention answers such needs.

SUMMARY OF THE INVENTION

The invention relates to a solid Δ⁹-THC composition comprising, consisting essentially of, or consisting of Δ⁹-THC and a powder former having a molar ratio of Δ⁹-THC to powder former to form a flowable Δ⁹-THC powder and where the powder former is selected from the group consisting of adenine, aspartame, caffeine, lactose, mannitol, nicotinamide, β-nicotinamide adenine dinucleotide, pipecolic acid, saccharin, aspartic acid, glutamic acid, glutamine, histidine, leucine, methionine, phenylalanine, proline, serine, tryptophan, valine, Epigallocatechin Gallate (EGCG), 2-Hydroxypropyl-beta-cyclodextrin (HPbCD), and Trimethyl-beta-cyclodextrin (TOMBC) and mixtures thereof. In some embodiments the molar ratio of Δ⁹-THC to powder former may range from about 4:1 to about 1:4, from about 3:1 to about 1:3, from about 2:1 to about 1:2 or may be about 1:1. In one solid Δ⁹-THC composition, the powder former is aspartame. In another the powder former is caffeine. And in another the powder former is L-valine.

The invention also relates to methods of making a solid Δ⁹-THC composition comprising, consisting essentially of, or consisting of the step of combining Δ⁹-THC with a powder former under conditions and in a molar ratio to form a flowable Δ⁹-THC powder, where the powder former is selected from the group consisting of adenine, aspartame, caffeine, lactose, mannitol, nicotinamide, β-nicotinamide adenine dinucleotide, pipecolic acid, saccharin, aspartic acid, glutamic acid, glutamine, histidine, leucine, methionine, phenylalanine, proline, serine, tryptophan, valine, Epigallocatechin Gallate (EGCG), 2-Hydroxypropyl-beta-cyclodextrin (HPbCD), and Trimethyl-beta-cyclodextrin (TOMBC) and mixtures thereof. One method of making a solid Δ⁹-THC composition comprises the steps of dissolving the Δ⁹-THC and the powder former in a solvent system to form a solution, and removing the solvent from the solution to yield a solid Δ⁹-THC composition. In a method or in a composition of the invention the Δ⁹-THC may be synthetic Δ⁹-THC or may be extracted Δ⁹-THC.

The invention provides pharmaceutical or nutraceutical composition comprising, consisting essentially of, or consisting of a solid Δ⁹-THC composition of the invention and a pharmaceutically- or nutraceutically-acceptable carrier, wherein Δ⁹-THC is present in the composition in a pharmaceutically or nutraceutically effective amount. The invention also provides methods of treating a disease, disorder, or condition comprising, consisting essentially of, or consisting of the step of administering to a patient in need thereof a therapeutically effective amount of a solid Δ⁹-THC composition according to the invention or of administering to a patient in need thereof a therapeutic composition containing a solid Δ⁹-THC composition.

A solid Δ⁹-THC composition may also be incorporated into food (edibles) and beverage products.

BRIEF DESCRIPTION OF THE FIGURES

FIG. 1 shows the X-ray powder diffraction (XRPD) pattern of a freeze-dried 1:1 Δ⁹-THC/Adenine powder.

FIG. 2 shows the X-ray powder diffraction (XRPD) pattern of a freeze-dried 1:1 Δ⁹-THC/Aspartame powder.

FIG. 3 shows the X-ray powder diffraction (XRPD) pattern of a freeze-dried 1:1 Δ⁹-THC/Caffeine powder.

FIG. 4 shows the X-ray powder diffraction (XRPD) pattern of a freeze-dried 1:1 Δ⁹-THC/Glutamine powder.

FIG. 5 shows the X-ray powder diffraction (XRPD) pattern of a freeze-dried 1:1 Δ⁹-THC/Histidine powder.

FIG. 6 shows the X-ray powder diffraction (XRPD) pattern of a freeze-dried 1:1 Δ⁹-THC/Lactose powder.

FIG. 7 shows the X-ray powder diffraction (XRPD) pattern of a freeze-dried 1:1 Δ⁹-THC/D-Mannitol powder.

FIG. 8 shows the X-ray powder diffraction (XRPD) pattern of a freeze-dried 1:1 Δ⁹-THC/Nicotinamide powder.

FIG. 9 shows the X-ray powder diffraction (XRPD) pattern of a freeze-dried 1:1 $\Delta^9$-THC/L-Pipecolic Acid powder.

FIG. 10 shows the X-ray powder diffraction (XRPD) pattern of a freeze-dried 1:1 $\Delta^9$-THC/Saccharin powder.

FIG. 11 shows the X-ray powder diffraction (XRPD) pattern of a freeze-dried 1:1 $\Delta^9$-THC/L-Tryptophan powder.

FIG. 12 shows the X-ray powder diffraction (XRPD) pattern of a freeze-dried 1:1 $\Delta^9$-THC/L-Valine powder.

FIG. 13 shows the X-ray powder diffraction (XRPD) pattern of a freeze-dried 1:4 $\Delta^9$-THC/L-Aspartic Acid powder.

FIG. 14 shows the X-ray powder diffraction (XRPD) pattern of a freeze-dried 1:4 $\Delta^9$-THC/L-Glutamic Acid powder.

FIG. 15 shows the X-ray powder diffraction (XRPD) pattern of a freeze-dried 1:4 $\Delta^9$-THC/L-Leucine powder.

FIG. 16 shows the X-ray powder diffraction (XRPD) pattern of a freeze-dried 1:4 $\Delta^9$-THC/L-Methionine powder.

FIG. 17 shows the X-ray powder diffraction (XRPD) pattern of a freeze-dried 1:4 $\Delta^9$-THC/β-nicotinamide Adenine Dinucleotide powder.

FIG. 18 shows the X-ray powder diffraction (XRPD) pattern of a freeze-dried 1:2 $\Delta^9$-THC/L-Phenylalanine powder.

FIG. 19 shows the X-ray powder diffraction (XRPD) pattern of a freeze-dried 1:4 $\Delta^9$-THC/L-Proline powder.

FIG. 20 shows the X-ray powder diffraction (XRPD) pattern of a freeze-dried 1:4 $\Delta^9$-THC/L-Serine powder.

FIG. 21 shows the X-ray powder diffraction (XRPD) pattern of a $\Delta^9$-THC/Aspartame 1:1 powder prepared by evaporation.

FIG. 22 shows the X-ray powder diffraction (XRPD) pattern of a $\Delta^9$-THC/Caffeine 1:1 powder prepared by evaporation.

FIG. 23 shows the X-ray powder diffraction (XRPD) pattern of a $\Delta^9$-THC/L-Pipecolic Acid 1:1 powder prepared by evaporation.

FIG. 24 shows the X-ray powder diffraction (XRPD) pattern of a $\Delta^9$-THC/Aspartame 1:1 powder prepared by physical mixing.

FIG. 25 shows the X-ray powder diffraction (XRPD) pattern of a $\Delta^9$-THC/Caffeine 1:1 powder prepared by physical mixing.

FIG. 26 shows the X-ray powder diffraction (XRPD) pattern of a $\Delta^9$-THC/Lactose 1:1 powder prepared by physical mixing.

FIG. 27 shows the X-ray powder diffraction (XRPD) pattern of a $\Delta^9$-THC/L-Pipecolic Acid 1:1 powder prepared by physical mixing.

FIG. 28 shows the X-ray powder diffraction (XRPD) pattern of a freeze-dried 2:1 $\Delta^9$-THC/EGCG powder.

FIG. 29 shows the X-ray powder diffraction (XRPD) pattern of a freeze-dried 1:2 $\Delta^9$-THC/L-glutamine powder.

FIG. 30 shows the X-ray powder diffraction (XRPD) pattern of a $\Delta^9$-THC/HPbCD 1:1 powder prepared by rotary evaporation.

FIG. 31 shows the X-ray powder diffraction (XRPD) pattern of a $\Delta^9$-THC/TOMBC 1:1 powder prepared by rotary evaporation.

FIG. 32 shows the X-ray powder diffraction (XRPD) pattern of a freeze-dried 1:2 $\Delta^9$-THC/Aspartame powder.

FIG. 33 shows the X-ray powder diffraction (XRPD) pattern of a freeze-dried 1:4 $\Delta^9$-THC/Aspartame powder.

FIG. 34 shows the X-ray powder diffraction (XRPD) pattern of a freeze-dried 2:1 $\Delta^9$-THC/Aspartame powder.

FIG. 35 shows the X-ray powder diffraction (XRPD) pattern of a freeze-dried 4:1 $\Delta^9$-THC/Aspartame powder.

FIG. 36 shows the X-ray powder diffraction (XRPD) pattern of a freeze-dried 1:2 $\Delta^9$-THC/L-Valine powder.

FIG. 37 shows the X-ray powder diffraction (XRPD) pattern of a freeze-dried 1:4 $\Delta^9$-THC/L-Valine powder.

FIG. 38 shows the X-ray powder diffraction (XRPD) pattern of a freeze-dried 2:1 $\Delta^9$-THC/L-Valine powder.

FIG. 39 shows the X-ray powder diffraction (XRPD) pattern of a freeze-dried 4:1 $\Delta^9$-THC/L-Valine powder.

FIG. 40 shows the X-ray powder diffraction (XRPD) pattern of a freeze-dried 1:2 $\Delta^9$-THC/Caffeine powder.

FIG. 41 shows the X-ray powder diffraction (XRPD) pattern of a freeze-dried 1:4 $\Delta^9$-THC/Caffeine powder.

DESCRIPTION OF THE INVENTION

Solid $\Delta^9$-THC Compositions

The invention relates to a solid $\Delta^9$-THC composition comprising, consisting essentially of, or consisting of $\Delta^9$-THC as a first component and a powder former as a second component. In a solid $\Delta^9$-THC composition of the invention the $\Delta^9$-THC and the powder former are present in a molar ratio of $\Delta^9$-THC to powder former to form a flowable $\Delta^9$-THC powder. A flowable powder is a solid composition of loose particulates that flow as a bulk property of the powder. In common terms, by way of illustration, the powder may flow through an orifice (e.g., sand through an hourglass) or may be poured (e.g., sugar from a packet). In some instances, a flowable powder may have a static or triboelectric charge that impacts its flow and may cause it to adhere to a surface.

In a solid $\Delta^9$-THC composition of the invention the powder former is selected from the group consisting of adenine, aspartame, caffeine, lactose, mannitol, nicotinamide, β-nicotinamide adenine dinucleotide, pipecolic acid, saccharin, aspartic acid, glutamic acid, glutamine, histidine, leucine, methionine, phenylalanine, proline, serine, tryptophan, valine, Epigallocatechin Gallate (EGCG), 2-Hydroxypropyl-beta-cyclodextrin (HPbCD), and Trimethyl-beta-cyclodextrin (TOM BC) and mixtures thereof. Each powder former may be used individually in a solid $\Delta^9$-THC composition of the invention. Combinations of two, three, four, five or more, up to a mixture of all powder formers, may be used solid $\Delta^9$-THC composition of the invention.

The powder formers include the amino acids aspartic acid, glutamic acid, glutamine, histidine, leucine, methionine, phenylalanine, proline, serine, tryptophan and valine which may be L-amino acids, D-amino acids or D,L-amino acids. The amino acid powder formers may be L-aspartic acid, L-glutamic acid, L-glutamine, L-histidine, L-leucine, L-methionine, L-phenylalanine, L-proline, L-serine, L-tryptophan, L-valine and mixtures thereof. When the powder former is pipecolic acid it may be L-pipecolic acid, D-pipecolic acid or D,L-pipecolic acid.

A solid $\Delta^9$-THC composition of the invention has $\Delta^9$-THC and the powder former combined in molar ratios of $\Delta^9$-THC to powder former which form a flowable $\Delta^9$-THC powder. Exemplary molar ratios of $\Delta^9$-THC to powder former may range from about 4:1 to about 1:4, may range from about 3:1 to about 1:3, may range from about 2:1 to about 1:2 or may be about 1:1. Solid $\Delta^9$-THC compositions of the invention are not limited to these exemplary molar ratios. Different powder formers may have different $\Delta^9$-THC to powder former molar ratios which yield a flowable $\Delta^9$-THC powder.

One solid $\Delta^9$-THC composition comprises $\Delta^9$-THC and a powder former having a molar ratio of $\Delta^9$-THC to powder former to form a flowable $\Delta^9$-THC powder and wherein the powder former is selected from the group consisting of aspartic acid, glutamic acid, glutamine, histidine, leucine, methionine, phenylalanine, proline, serine, tryptophan, valine and mixtures thereof. Exemplary molar ratios of $\Delta^9$-THC to powder former may range from about 4:1 to about 1:4, may range from about 3:1 to about 1:3, may range from about 2:1 to about 1:2 or may be about 1:1.

A solid $\Delta^9$-THC composition of the invention comprises $\Delta^9$-THC and L-valine as the powder former and has a molar ratio of $\Delta^9$-THC to powder former to form a flowable $\Delta^9$-THC powder. Exemplary molar ratios of $\Delta^9$-THC to the L-valine powder former may range from about 4:1 to about 1:4, may range from about 3:1 to about 1:3, may range from about 2:1 to about 1:2 or may be about 1:1.

Another solid $\Delta^9$-THC composition of the invention comprises $\Delta^9$-THC and aspartame as the powder former and has a molar ratio of $\Delta^9$-THC to powder former to form a flowable $\Delta^9$-THC powder. Exemplary molar ratio of $\Delta^9$-THC to the aspartame powder former may range from about 4:1 to about 1:4, may range from about 3:1 to about 1:3, may range from about 2:1 to about 1:2 or may be about 1:1.

One other solid $\Delta^9$-THC composition of the invention comprises $\Delta^9$-THC and caffeine as the powder former and has a molar ratio of $\Delta^9$-THC to powder former to form a flowable $\Delta^9$-THC powder. Exemplary molar ratios of $\Delta^9$-THC to the caffeine powder former may range from about 1:1 to about 1:4, may range from about 1:1 to about 1:3, may range from about 1:1 to about 1:2 or may be about 1:1.

Methods of Making Solid $\Delta^9$-THC Compositions

A solid $\Delta^9$-THC composition of the invention may be made by a variety of methods known in the art which combine $\Delta^9$-THC and a powder former according to the invention. For example, a solid $\Delta^9$-THC composition may be made by lyophilizing (freeze drying) a solution of $\Delta^9$-THC and a powder former or by slow or rotary evaporation of the solvent from the solution. A solid $\Delta^9$-THC composition of the invention may also be made by simple mixing of $\Delta^9$-THC and a powder former. Accordingly, the invention relates to a method of making a solid $\Delta^9$-THC composition by combining $\Delta^9$-THC with a powder former under conditions to form a flowable $\Delta^9$-THC powder. The $\Delta^9$-THC and the powder former are combined in a molar ratio of $\Delta^9$-THC to powder former which form a flowable $\Delta^9$-THC powder. Exemplary molar ratios have been discussed above and are shown in the examples below.

The invention relates to a method of making a solid $\Delta^9$-THC composition by dissolving $\Delta^9$-THC and a powder former in a solvent system to form a solution. If the $\Delta^9$-THC and powder former are first dissolved separately then the solutions may be combined to form a solution containing both $\Delta^9$-THC and the powder former. The $\Delta^9$-THC and the powder former are present in the solution in a molar ratio of $\Delta^9$-THC to powder former which form a flowable $\Delta^9$-THC powder once the solvent is removed. The solvent is then removed from the solution, for example by lyophilization or by evaporation, to yield a flowable powder. Solvents that dissolve both the $\Delta^9$-THC and the powder former may be used as well as mixtures of solvents such that the $\Delta^9$-THC and powder former remain in solution. Suitable solvents include, for example, dioxane, dimethylsulfoxide (DMSO), N,N-dimethylformamide (DMF), acetonitrile, ethyl acetate, and $C_2$-$C_4$ alcohols (ethanol, propanol and the like). Water may be used but should be miscible with the solvent used to dissolve the $\Delta^9$-THC and not so much as to cause precipitation of the $\Delta^9$-THC from the solution.

A $\Delta^9$-THC powder composition of the invention may also be made by combining synthetic $\Delta^9$-THC and a powder former as just described in a molar ratio of $\Delta^9$-THC to powder former to form a flowable $\Delta^9$-THC powder. Alternatively, a $\Delta^9$-THC powder composition of the invention may also be made by combining extracted $\Delta^9$-THC and a powder former as just described in a molar ratio of $\Delta^9$-THC to powder former to form a flowable $\Delta^9$-THC powder.

In one method of the invention (+)-p-Menth-2-ene-1,8-diol is reacted with olivetol to prepare synthetic delta-9-tetrahydrocannabinol ($\Delta^9$-THC). See US 2007/0287843 which is incorporated by reference. (+)-p-Menth-2-ene-1,8-diol may be prepared from a reaction mixture including 2-carene epoxide, a solvent in which (+)-p-Menth-2-ene-1, 8-diol is insoluble, water, and an acid catalyst. Id. at ¶[0013]. (+)-p-Menth-2-ene-1,8-diol can also be prepared by mixing 2-carene epoxide and 3-carene epoxide, a solvent in which (+)-p-Menth-2-ene-1,8-diol is insoluble, water, and an acid catalyst. Id. at ¶[0014]. Therefore, $\Delta^9$-THC can be synthesized when cyclic compounds prepared from 2-carene, or cyclic compounds prepared from mixtures of 2-carene and 3-carene, are reacted with unsubstituted resorcinol or a substituted resorcinol (such as olivetol). Id. at ¶[0015]. The resulting synthetic $\Delta^9$-THC is then combined with a powder former selected from the group consisting of adenine, aspartame, caffeine, glutamine, histidine, lactose, mannitol, nicotinamide, pipecolic acid, saccharin, tryptophan, valine, Epigallocatechin Gallate (EGCG), 2-Hydroxypropyl-beta-cyclodextrin (HPbCD), and Trimethyl-beta-cyclodextrin (TOMBC) and mixtures thereof using a method such as those described above. For example, by combination in a solvent system to form a solution where the solvent is then removed from the solution to yield a THC powder.

Another method of the invention prepares synthetic $\Delta^9$-THC in a "one-pot" condensation and sulfonylation reaction sequence which first produces a crude $\Delta^9$-THC aryl sulfonate ester, which is then hydrolyzed to produce synthetic $\Delta^9$-THC. See WO 2009/099868 which is incorporated by reference. $\Delta^9$-THC can be synthesized by condensing a substituted resorcinol compound in the presence of an acid catalyst and a non-alkaline dehydrating agent. Id. at ¶[0017]. After completion of the condensation reaction, the reaction mixture is sulfonated by treating the reaction mixture with an aryl sulfonyl halide in the presence of a base to produce an aryl sulfonate. Id. at ¶[0019]. The isolated aryl sulfonate is then hydrolyzed to form synthetic $\Delta^9$-THC. Id. at ¶[0020]. The resulting synthetic $\Delta^9$-THC is then combined with a powder former selected from the group consisting of adenine, aspartame, caffeine, glutamine, histidine, lactose, mannitol, nicotinamide, pipecolic acid, saccharin, tryptophan, valine, Epigallocatechin Gallate (EGCG), 2-Hydroxypropyl-beta-cyclodextrin (HPbCD), and Trimethyl-beta-cyclodextrin (TOMBC) and mixtures thereof using a method such as those described above. For example, by combination in a solvent system to form a solution where the solvent is then removed from the solution to yield a THC powder.

In one method of the invention synthetic $\Delta^9$-THC is prepared by treating a first intermediate compound with an organoaluminum-based Lewis acid catalyst. See WO 2007/041167, which is incorporated by reference. The first intermediate compound is a compound of formula I:

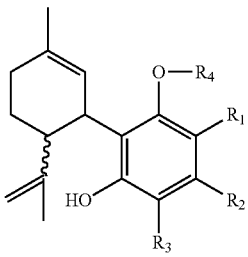

(I)

where:
- R₁ is H, substituted or unsubstituted alkyl, carboxylic ester, or acyl;
- R₂ is H, OH, protected hydroxyl, substituted or unsubstituted alkyl, alkenyl, alkynyl, acyl, aryl, or heteroaryl;
- R₃ is H, substituted or unsubstituted alkyl, carboxylic ester, or acyl; and
- R₄ is H, substituted or unsubstituted alkyl, silyl, heterosubstituted or unsubstituted acyl, alkylsulfonyl, arylsulfonyl, alkylphosphoryl, or arylphosphoryl. Id. pg. 2 line 29-pg. 3 line 9. The resulting synthetic $\Delta^9$-THC is then combined with a powder former selected from the group consisting of adenine, aspartame, caffeine, glutamine, histidine, lactose, mannitol, nicotinamide, pipecolic acid, saccharin, tryptophan, valine, Epigallocatechin Gallate (EGCG), 2-Hydroxypropyl-beta-cyclodextrin (HPbCD), and Trimethyl-beta-cyclodextrin (TOMBC) and mixtures thereof using a method such as those described above. For example, by combination in a solvent system to form a solution where the solvent is then removed from the solution to yield a $\Delta^9$-THC powder.

In another method of the invention, 6, 12-dihydro-6-hydroxy-cannabidiol is subjected to ring condensation to prepare synthetic $\Delta^9$-THC. See EP 0494665, which is incorporated by reference. The ring condensation is performed in a solvent selected from the group consisting of hydrocarbons, aromatic hydrocarbons, and chlorinated hydrocarbons. Id. at claim 9. The resulting synthetic $\Delta^9$-THC is then combined with a powder former selected from the group consisting of adenine, aspartame, caffeine, glutamine, histidine, lactose, mannitol, nicotinamide, pipecolic acid, saccharin, tryptophan, valine, Epigallocatechin Gallate (EGCG), 2-Hydroxypropyl-beta-cyclodextrin (HPbCD), and Trimethyl-beta-cyclodextrin (TOMBC) and mixtures thereof using a method such as those described above. For example, by combination in a solvent system to form a solution where the solvent is then removed from the solution to yield a $\Delta^9$-THC powder.

In another method of the invention, cannabidiol (CBD) is present in an organic solvent and cyclized to prepare synthetic $\Delta^9$-THC in the presence of a molecular sieve while being heated. See U.S. Pat. No. 8,324,408, which is incorporated by reference. The CBD dissolved in an organic solvent is contacted with the molecular sieve while being boiled under reflux. Id. at claim 2. The resulting synthetic $\Delta^9$-THC is then combined with a powder former selected from the group consisting of adenine, aspartame, caffeine, glutamine, histidine, lactose, mannitol, nicotinamide, pipecolic acid, saccharin, tryptophan, valine, Epigallocatechin Gallate (EGCG), 2-Hydroxypropyl-beta-cyclodextrin (HPbCD), and Trimethyl-beta-cyclodextrin (TOMBC) and mixtures thereof using a method such as those described above. For example, by combination in a solvent system to form a solution where the solvent is then removed from the solution to yield a $\Delta^9$-THC powder.

In another method of the invention, synthetic $\Delta^9$-THC is prepared from CBD. See WO 2002/070506, which is incorporated by reference. A catalyst is added to a reaction mixture comprising CBD in an organic solvent under a nitrogen atmosphere. Id. at 3. NaHCO₃ is added to the reaction mixture and stirred. Id. at 4. The mixture is allowed to separate into an aqueous phase and an organic phase. Id. The organic phase is removed and the $\Delta^9$-THC is eluted from the organic phase. Id. The resulting synthetic $\Delta^9$-THC is then combined with a powder former selected from the group consisting of adenine, aspartame, caffeine, glutamine, histidine, lactose, mannitol, nicotinamide, pipecolic acid, saccharin, tryptophan, valine, Epigallocatechin Gallate (EGCG), 2-Hydroxypropyl-beta-cyclodextrin (HPbCD), and Trimethyl-beta-cyclodextrin (TOMBC) and mixtures thereof using a method such as those described above. For example, by combination in a solvent system to form a solution where the solvent is then removed from the solution to yield a $\Delta^9$-THC powder.

In one method of the invention $\Delta^9$-THC is extracted from plant material with a non-polar solvent followed by vacuum distillation and chromatography. See U.S. Pat. No. 6,365,416 which is incorporated by reference. The *Cannabis* plant material is extracted with a non-polar organic solvent to form an extract. Id. at Claim 1. The solvent is removed from the extract resulting in an extract residue. Id. The extract residue is subjected to a first low-pressure flash distillation where the first distillate contains $\Delta^9$-THC. Id. The first distillate can be subjected to a second low pressure flash distillation to produce a second distillate containing $\Delta^9$-THC. Id. The first and second distillate are subjected to column chromatography, normal HPLC, or reversed HPLC to result in a product containing $\Delta^9$-THC. Id. The extracted THC is then combined with a powder former selected from the group consisting of adenine, aspartame, caffeine, glutamine, histidine, lactose, mannitol, nicotinamide, pipecolic acid, saccharin, tryptophan, valine, Epigallocatechin Gallate (EGCG), 2-Hydroxypropyl-beta-cyclodextrin (HPbCD), and Trimethyl-beta-cyclodextrin (TOMBC) and mixtures thereof using a method such as those described above. For example, by combination in a solvent system to form a solution where the solvent is then removed from the solution to yield a $\Delta^9$-THC powder.

In another method of the invention, $\Delta^9$-THC is extracted from *cannabis* plants using supercritical fluid. See, e.g., US 2003/0050334 and WO 2020/102898 which are both incorporated by reference. The plant is subjected to a supercritical fluid, preferably liquid CO₂, either alone or in combination with other cosolvents to extract the $\Delta^9$-THC. See US 2003/0050334 at ¶[0053]. The extraction occurs at a temperature >65° C. for selectively extracting $\Delta^9$-THC over CBD from the plant material. See WO 2020/102898 at claim 1. The extracted $\Delta^9$-THC is then combined with a powder former selected from the group consisting of adenine, aspartame, caffeine, glutamine, histidine, lactose, mannitol, nicotinamide, pipecolic acid, saccharin, tryptophan, valine, Epigallocatechin Gallate (EGCG), 2-Hydroxypropyl-beta-cyclodextrin (HPbCD), and Trimethyl-beta-cyclodextrin (TOMBC) mixtures thereof using a method such as those described above. For example, by combination in a solvent system to form a solution where the solvent is then removed from the solution to yield a $\Delta^9$-THC powder.

In another method of the invention, $\Delta^9$-THC is extracted from a *cannabis* plant by irradiating microwaves to a reaction mixture comprising a CBD-comprising sample, a Lewis acid, and a solvent in an airtight container. See US 2021/0002247 which is incorporated by reference. The extracted $\Delta^9$-THC is then combined with a powder former selected from the group consisting of adenine, aspartame, caffeine, glutamine, histidine, lactose, mannitol, nicotinamide, pipecolic acid, saccharin, tryptophan, valine, Epigallocatechin Gallate (EGCG), 2-Hydroxypropyl-beta-cyclodextrin (HPbCD), and Trimethyl-beta-cyclodextrin (TOMBC) mixtures thereof using a method such as those described above. For example, by combination in a solvent system to form a solution where the solvent is then removed from the solution to yield a $\Delta^9$-THC powder.

Uses of Solid $\Delta^9$-THC Compositions

As discussed above $\Delta^9$-THC is known in the art to be useful in the treatment of various diseases, disorders, and conditions. The solid $\Delta^9$-THC compositions of the invention, and pharmaceutical compositions containing them may then also be used to treat such diseases, disorders, and conditions. The diseases, disorders or conditions which may be treated with a solid $\Delta^9$-THC composition of the invention include, but are not limited to: pain (including but not limited to acute pain; chronic pain; neuropathic pain and cancer pain), neurodegenerative disease (including but not limited to Alzheimer's disease; Parkinson's disease; amyotrophic lateral sclerosis; Huntington's disease; multiple sclerosis; frontotemporal dementia; prion disease; Lewy body dementia; progressive supranuclear palsy; vascular dementia; normal pressure hydrocephalus; traumatic spinal cord injury; HIV dementia; alcohol induced neurotoxicity; Down's syndrome; epilepsy or any other related neurological or psychiatric neurodegenerative disease), inflammatory or autoimmune disease, fibrosis, cancer, nausea and vomiting, diabetes, adiposity and metabolic syndrome.

Accordingly, the invention relates to the method of treating such a disease, disorder, or condition comprising, consisting essentially of, or consisting of the step of administering to a patient in need thereof a therapeutically effective amount of a solid $\Delta^9$-THC composition of the invention or of administering to a patient in need thereof a therapeutic composition containing a solid $\Delta^9$-THC composition of the invention.

The term "treatment" or "treating" means any treatment of a disease, disorder or condition in a mammal, including: preventing or protecting against the disease, disorder or condition, that is, causing the clinical symptoms not to develop; inhibiting the disease, disorder or condition, that is, arresting or suppressing the development of clinical symptoms; and/or relieving the disease, disorder or condition (including the relief of discomfort associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the disease, disorder or condition. The term "protection" is meant to include "prophylaxis."

Another aspect of the invention relates to the use of a solid $\Delta^9$-THC composition of the invention in the treatment of diseases, disorders and conditions discussed above. Accordingly, the invention further relates to the manufacture of a medicament for use in the treatment of such diseases, disorders and conditions.

Compositions Containing Solid $\Delta^9$-THC Compositions

The invention relates to a pharmaceutical or nutraceutical composition containing a solid $\Delta^9$-THC composition of the invention and a pharmaceutically- or nutraceutically-acceptable carrier. A pharmaceutical or nutraceutical composition includes vitamin compositions. The solid $\Delta^9$-THC composition may be present as a flowable powder and may be mixed with the carrier. $\Delta^9$-THC is present in the composition in a pharmaceutically- or nutraceutically-effective amount. As mentioned above, these pharmaceutical compositions are therapeutically useful to treat or prevent disorders such as those discussed above. Such a composition of the invention may be a solid dosage form or a solution made with a solid $\Delta^9$-THC composition of the invention.

A composition of the invention may be in any pharmaceutical or nutraceutical form which contains a solid $\Delta^9$-THC composition according to the invention. The composition may be, for example, a tablet, a capsule, a consumable formulation, an injectable composition, a topical composition, an inhalable composition or a transdermal composition.

The compositions generally contain, for example, about 0.1% to about 99.9% by weight of a solid $\Delta^9$-THC composition of the invention, for example, about 0.5% to about 99% by weight of a solid $\Delta^9$-THC composition of the invention and, for example, 99.5% to 0.5% by weight of at least one suitable pharmaceutical excipient or solvent. In one embodiment, the composition may be between about 5% and about 75% by weight of a solid $\Delta^9$-THC composition of the invention with the rest being at least one suitable pharmaceutical excipient, solvent or at least one other adjuvant, as discussed below.

A "therapeutically effective amount of $\Delta^9$-THC according to the invention" is that which correlates to a therapeutic effect and may for example, be about 5 mg-about 2,000 mg, about 50 mg-about 1500 mg, about 100 mg-about 1000 mg, about 250 mg-about 750 mg, or about 500 mg. The actual amount required for treatment of any particular disease, disorder or condition for any particular patient may depend upon a variety of factors including, for example, the particular disease, disorder or condition being treated; the disease state being treated and its severity; the specific pharmaceutical composition employed; the age, body weight, general health, sex and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference.

Depending on the type of composition, the pharmaceutically-acceptable or nutraceutically-acceptable carrier may be chosen from any one or a combination of carriers known in the art. The choice of carrier depends upon the pharmaceutical or nutraceutical form and the desired method of administration to be used. The carrier should not substantially alter the solid $\Delta^9$-THC composition, for example, such that the solid $\Delta^9$-THC composition becomes tacky or the $\Delta^9$-THC component becomes oily. Nor should the carrier be otherwise incompatible with a solid $\Delta^9$-THC composition used, such as by producing any undesirable biological effect or otherwise interacting in a deleterious manner with any other component(s) of the pharmaceutical or nutraceutical composition.

The pharmaceutical or nutraceutical compositions of the invention may be prepared by methods known in the formulation art, for example, see Remington's Pharmaceutical Sciences, 18th Ed., (Mack Publishing Company, Easton, Pa., 1990), which is incorporated herein by reference. In a solid dosage form, a solid $\Delta^9$-THC composition of the invention may be admixed with at least one pharmaceutically-acceptable or nutraceutically-acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically-acceptable and nutraceutically-acceptable adjuvants known in the pharmaceutical and nutraceutical formulation art may also be used in the pharmaceutical or nutraceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others, as is known in the pharmaceutical or nutraceutical art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that may be prepared by mixing a solid $\Delta^9$-THC composition of the invention with, for example, suitable non-irritating excipients or carriers such as cocoa butter, polyethyleneglycol or a suppository wax, which may be solid at ordinary temperatures but may be liquid at body temperature and, therefore, melt while in a suitable body cavity and release the active component therein.

Compositions suitable for topical administration include liquid or semi-liquid preparations such as liniments, lotions, gels, applicants, oil-in-water or water-in-oil emulsions such as creams, ointments, pastes or foams; or solutions or suspensions such as drops, as is known in the art. Compositions of the invention may be intended for topical administration, in which case the carrier may suitably comprise a solution, emulsion, ointment or gel base. The carrier or base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

In addition to the topical method of administration described above, there are various methods of administering the active a solid $\Delta^9$-THC composition of the invention topically to the lung. One such means could involve a dry powder inhaler formulation of respirable particles comprised of a solid $\Delta^9$-THC composition of the invention, which the patient being treated inhales. It is common for a dry powder formulation to include carrier particles, to which the solid $\Delta^9$-THC composition particles can adhere to. The carrier particles may be of any acceptable pharmacologically inert material or combination of materials. For example, the carrier particles may be composed of one or more materials selected from sugar alcohols; polyols, for example sorbitol, mannitol or xylitol, and crystalline sugars, including monosaccharides and disaccharides; inorganic salts such as sodium chloride and calcium carbonate; organic salts such as sodium lactate; and other organic compounds such as urea, polysaccharides, for example cyclodextrins and dextrins. The carrier particles may be a crystalline sugar, for example, a monosaccharide such as glucose or arabinose, or a disaccharide such as maltose, saccharose, dextrose or lactose.

In addition to the topical method of administration described above, there are various methods of administering the active a solid $\Delta^9$-THC composition of the invention systemically by such methods. One such means would involve an aerosol suspension of respirable particles comprised of a solid $\Delta^9$-THC composition of the invention, which the patient being treated inhales. A solid $\Delta^9$-THC composition would be absorbed into the bloodstream via the lungs in a pharmaceutically effective amount. The respirable particles can be liquid or solid, with a particle size sufficiently small to pass through the mouth and larynx upon inhalation.

Because the solid $\Delta^9$-THC composition may be maintained during preparation, solid dosage forms are one embodiment of the pharmaceutical composition of the invention. Dosage forms for oral administration, which includes capsules, tablets, pills, powders, granules, and suspensions may be used. Dosage forms for pulmonary administration, which includes metered dose inhaler, dry powder inhaler or aerosol formulations may be used. In such solid dosage forms, the active compound may be mixed with at least one inert, pharmaceutically-acceptable or nutraceutically-acceptable excipient (also known as a pharmaceutically-acceptable or nutraceutically-acceptable carrier).

Edible Compositions

A solid $\Delta^9$-THC composition of the invention may also be incorporated into an edible composition such as food products and beverages. The food products may be prepared food products such as cakes, candy, breads, etc. or mixes used to prepare such products. The food product may also be a tea or a coffee used to prepare a tea or coffee beverage. The beverage product may be a ready-to-drink beverage such as soda, tea, coffee, juices, sports drinks, beer, etc. The food product or beverage may be for human or animal consumption.

EXAMPLES

X-ray Powder Diffraction (XRPD) for Examples 1-3 and 6: A Rigaku Smart-Lab X-ray diffraction system was configured for reflection BraggBrentano geometry using a line source X-ray beam. The x-ray source is a Cu Long Fine Focus tube that was operated at 40 kV and 44 mA. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1 °2θ or less. The axial divergence of the X-ray beam is controlled by 5.0-degree Soller slits in both the incident and diffracted beam paths. Powder samples were prepared in a low background Si holder using light manual pressure to keep the sample surfaces flat and level with the reference surface of the sample holder. Each sample was analyzed from 2 to 40 °2θ using a continuous scan of 6 °2θ per minute with an effective step size of 0.02 °2θ.

X-ray Powder Diffraction (XRPD) for Examples 4 and 5: XRPD patterns were also collected with a PANalytical X'Pert PRO MPD or a PANalytical Empyrean diffractometer using an incident beam of Cu radiation produced using an Optix long, fine-focus source. An elliptically graded multi-layer mirror was used to focus Cu Kα X-rays through the specimen and onto the detector. Prior to the analysis, a silicon specimen (NIST SRM 640f) was analyzed to verify the observed position of the Si 111 peak is consistent with the NIST-certified position. A specimen of the sample was sandwiched between 3 μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 5.5.

Example 1: Solid $\Delta^9$-THC Compositions by Freeze-Drying (Lyophilization)

A commercially available $\Delta^9$-THC-acetonitrile solution (Cayman Chemical), approximately 50 mg $\Delta^9$-THC per mL, was used. The actual concentration was determined gravimetrically by taring a vial and recording its weight, adding 1 mL of solution, evaporating the solution, vacuum drying the sample at room temperature for 12 hours and reweighing the vial. The actual concentration was determined to be 51 mg/mL. Into 1 dram vials, 300 μl of the $\Delta^9$-THC acetonitrile solution was dispensed and allowed to evaporate at room temperature resulting in each vial containing ca. 15.3 mg of $\Delta^9$-THC.

$\Delta^9$-THC (ca. 15.3 mg) was dissolved in dioxane (3 mL solvent used) and transferred into a 25 mL round bottom flask. The powder former (amount based on 1:1, 1:2 or 1:4 molar $\Delta^9$-THC:powder former ratio) was dissolved in $H_2O$ (2 mL) and, if needed, dioxane (2 mL) was added to form a solution. The powder former solution was added to the $\Delta^9$-THC solution in the round bottom flask. The round bottom flask was then submerged in a dry ice/acetone bath or liquid nitrogen to freeze the solution while continuously rotating the flask by hand to maximize surface area and form an even, thin layer around the flask. Once frozen, the round bottom flask was attached to a LabConco lyophilizer with an Edwards RV8 vacuum pump pre-equilibrated at ~−50° C. Samples were left overnight (18 hrs) and removed the next day.

$\Delta^9$-THC and several powder formers were lyophilized using the described procedure to determine if a flowable powder would result. Experiments using L-asparagine, L-leucine, and L-aspartic acid required heating at ~45° C. overnight to obtain a clear solution. In these cases, the solution of powder former was added to the $\Delta^9$-THC solution while still hot. To minimize the risk of precipitation, the round bottom flask was quickly submerged in either a dry ice/acetone bath or liquid nitrogen to freeze the solution.

Lyophilizing $\Delta^9$-THC according to the same procedure, without a powder former, from dioxane alone resulted in a gel and from dioxane/water (~75/25 by volume) resulted in a tacky gel. Proton ($^1$H) NMR analysis of the flowable powders showed the THC present to be $\Delta^9$-THC. A sampling of the $\Delta^9$-THC:powder former flowable powders were stored at sub-ambient temperatures (~−18° C.) for 21-30 days and observed to see if a flowable powder remained. A sampling of the $\Delta^9$-THC flowable powders were then left at ambient temperature and again observed to see if a flowable powder remained. These results are also shown in Table 1 and Table 2.

TABLE 1

| Powder former | $\Delta^9$-THC:Powder former ratio | Flowable powder | Flowable solids - sub-ambient temp. | Flowable solids - ambient temp. (minimum 30 days) |
|---|---|---|---|---|
| Adenine | 1:1 | Yes | Yes | Yes - Dark beige color |
| Aspartame | 1:1 | Yes | Yes | Yes -Light beige color |
| Caffeine | 1:1 | Yes | Yes | Yes -Light beige color |
| Glutamine | 1:1 | Yes | Yes | Yes - Light beige color |
| Histidine | 1:1 | Yes | Yes | Yes - Dark beige color |
| Lactose | 1:1 | Yes | Yes | Yes - Light beige color |
| D-Mannitol | 1:1 | Yes | Yes | Yes -Dark beige color |

TABLE 1-continued

| Powder former | Δ⁹-THC:Powder former ratio | Flowable powder | Flowable solids - sub-ambient temp. | Flowable solids - ambient temp. (minimum 30 days) |
|---|---|---|---|---|
| Nicotinamide | 1:1 | Yes | Yes | No - Red/brown tacky solid |
| L-Pipecolic acid | 1:1 | Yes | Yes - light beige | Yes - Brown color |
| Saccharin | 1:1 | Yes | Yes | Yes - Dark beige color |
| L-Tryptophan | 1:1 | Yes | Yes | Yes - Light beige color |
| L-Valine | 1:1 | Yes | Yes | Yes - Light beige color |
| L-Arginine | 1:1 | No -Gel/tacky solid | | |
| L-Ascorbic acid | 1:1 | No -Tacky solid | | |
| D-Fructose | 1:1 | No - Tacky solid | | |
| Glycine | 1:1 | No -Tacky solid | | |
| Glycolic acid | 1:1 | No -Tacky gel | | |
| L-Lactic acid | 1:1 | No -Gel | | |
| Nicotinic acid | 1:1 | No -Gel | | |
| Propyl gallate | 1:1 | No -Gel | | |
| Salicylic acid | 1:1 | No -Gel | | |
| Sucralose | 1:1 | No -Tacky solid | | |
| Sucrose | 1:1 | No - Tacky solid | | |
| Urea | 1:1 | No - Tacky solid | | |
| Vanillic acid | 1:1 | No - Gummy solid | | |
| Vanillin | 1:1 | No - Gel | | |

TABLE 2

| Powder former | Δ9-THC:Powder former ratio | Flowable solids - ambient temp. |
|---|---|---|
| L-Aspartic acid | 1:4 | Yes - Tan color |
| L-Glutamic acid | 1:4 | Yes - Yellow and white color |
| L-Leucine | 1:4 | Yes - Yellow and white color |
| L-Methionine | 1:4 | Yes - Yellow and white color |
| L-Phenylalanine | 1:2 | Yes - White color |
| L-Proline | 1:4 | Yes - Light orange color |
| L-Serine | 1:4 | Yes - Yellow and white color |
| β-Nicotinamide adenine dinucleotide | 1:4 | Yes - White color |
| L-Alanine | 1:2 | No - Tacky |
| L-Asparagine | 1:4 | No - Tacky yellow color |
| L-Lysine | 1:2 | No - Tacky gel |
| L-Lysine | 1:4 | No - Tacky |
| L-Proline | 1:2 | No - Gel |
| L-Threonine | 1:4 | No - Tacky |
| β-nicotinamide mononucleotide | 1:1 | No - Tacky |
| Nicotinamide riboside chloride | 1:4 | No - Tacky gel |

The flowable powders were characterized using a Rigaku Smart-Lab X-ray diffraction system and their X-ray powder diffraction (XRPD) patterns are shown in FIGS. 1-20. The Δ⁹-THC/Aspartame powder (FIG. 2), Δ⁹-THC/lactose powder (FIG. 6) and Δ⁹-THC/β-nicotinamide Adenine Dinucleotide powder (FIG. 17) showed only an amorphous halo. The XRPD patterns for each powder sample showed the presence of some powder former and an amorphous halo.

Example 2: Solid Δ⁹-THC Compositions by Evaporation

Δ⁹-THC (ca. 15.3 mg, prepared as in Example 1) was dissolved in methanol (MeOH) (1 mL). A powder former (amount based on a 1:1 Δ⁹-THC:powder former molar ratio) was added to the solution. If needed, additional MeOH (1-3 mL) was added until solids dissolved completely. The vial was left uncapped for fast evaporation (FE) at ambient temperature. The powder formers used were aspartame, caffeine, histidine, lactose and L-pipecolic acid. The Δ⁹-THC/histidine mixture resulted in a gel after evaporation. The other Δ⁹-THC/powder former mixtures were flowable powders and remained flowable powders when left at ambient temperature. The XRPD patterns were obtained for the Δ⁹-THC/aspartame powder (FIG. 21), Δ⁹-THC/caffeine powder (FIG. 22), and Δ⁹-THC/L-pipecolic acid powder (FIG. 23). Each XRPD pattern showed the presence of some crystalline powder former and an amorphous halo.

Example 3: Solid Δ⁹-THC Compositions by Physical Mixing

Δ⁹-THC (ca. 15.3 mg, prepared as in Example 1) and a powder former (amount based on 1:1 Δ⁹-THC:powder former molar ratio) were placed in a 1 dram vial. The solids were mixed with a glass stir rod and metal spatula. The powder formers used were aspartame, caffeine, histidine, lactose and L-pipecolic acid. The resulting material was a powder. The resulting materials were flowable powders and remained flowable powders when left at ambient temperature. The Δ⁹-THC/histidine mixture resulted in a tacky solid. The XRPD patterns were obtained for the Δ⁹-THC/aspartame powder (FIG. 24), the Δ⁹-THC/caffeine powder (FIG. 25), the Δ⁹-THC/lactose powder (FIG. 26), and the Δ⁹-THC/L-pipecolic acid powder (FIG. 27). The XRPD patterns showed the presence of some crystalline powder former and an amorphous halo.

Example 4: Solid Δ⁹-THC Compositions by Freeze-Drying (Lyophilization)

One capsule of Teavigo (Healthy Origins, 94% epigallocatechin gallate, EGCG) was emptied into a vial (net weight 207.7 mg; epigallocatechin gallate content 195.2 mg). Water (1 mL) was added and the mixture was stirred for approximately 30 minutes, affording a thick pink suspension. The suspension was filtered through a 0.2 μm nylon filter into a clean vial, resulting in a clear pink solution. Epigallocatechin gallate content was not confirmed in the solution.

A portion of the epigallocatechin gallate aqueous solution (374 μL) was combined with a solution of Δ⁹-THC in acetonitrile (1 mL of 50 mg/mL solution, Cayman Chemicals), affording a clear, slightly pinkish-brown solution. The solution was stirred at ambient temperature for 1 day and then evaporated from a vial covered with perforated foil in a jar under nitrogen gas flow. A clear, brown, sticky oil resulted. Tert-butanol (1 mL) and water (200 μL) were added to the oil with sonication, giving a clear orange solution. The solution was frozen in a thin layer on the walls of the vial by rotating in a bath of dry ice and isopropanol, and the vial was placed in a jar and attached to a Labconco FreeZone 2.5 Liter −84° C. Benchtop Freeze Dryer at −87.1° C. and 0.159 torr. After one day, the sample was removed and free-flowing, fluffy, light pink, non-birefringent solids were observed. The XRPD pattern was obtained for the 2:1Δ$^9$-THC/EGCG powder showing 2 amorphous halos (FIG. 28).

A solution of Δ$^9$-THC in acetonitrile (1 mL of 50 mg/mL solution, Cayman Chemicals) was added to a clean vial, stored in a freezer for approximately 1 month, and evaporated under a stream of nitrogen gas, forming a brown oil. The oil was dissolved in tert-butanol (2 mL) with sonication. Two molar equivalents of L-glutamine (45.8 mg, Sigma-Aldrich) were dissolved in water (2 mL) with sonication. The L-glutamine solution was added to the Δ$^9$-THC solution with stirring, and precipitation was observed. Additional water (2 mL) and tert-butanol (2 mL) were added, affording a clear solution. The solution was frozen in a thin layer on the walls of a flask by rotating in a bath of dry ice and isopropanol, and the flask was placed in a jar and attached to a Labconco FreeZone 2.5 Liter −84° C. Benchtop Freeze Dryer at −86.9° C. and ~0.2 torr. After one day, the sample was removed and free-flowing, fluffy, very light purple, non-birefringent solids were observed. The XRPD pattern of the 2:1 Δ$^9$-THC/L-glutamine powder showed the presence of some crystalline powder former and an amorphous halo (FIG. 29).

Example 5: Solid Δ$^9$-THC Compositions by Rotary Evaporation

A solution of Δ$^9$-THC in acetonitrile (1 mL of 50 mg/mL solution, Cayman Chemicals) was added to a clean vial. One molar equivalent of hydroxypropyl-β-cyclodextrin (HPbCD) (248.4 mg, TCI America) was added, producing a slurry. Methanol (3 mL) was added with sonication, and a clear pale yellow solution was observed. The solution was rotary evaporated (Buchi Rotavapor R-114) with a water bath temperature of 55° C. for approximately 2 minutes. White solids lined the vial, and no oil was visible. The sample was placed in a vacuum oven at ambient temperature for 1 day affording a free-flowing, off-white powder that was opaque and non-birefringent. The XRPD pattern was obtained for the 1:1 Δ$^9$-THC/hydroxypropyl-β-cyclodextrin (HPbCD) powder showing amorphous halos (FIG. 30)

A solution of Δ$^9$-THC in acetonitrile (1 mL of 50 mg/mL solution, Cayman Chemicals) was added to a clean vial. One molar equivalent of trimethyl-β-cyclodextrin (TOMBC) (227.4 mg, TCI America) was added, producing a clear solution. The solution was rotary evaporated (Buchi Rotavapor R-114) at ambient temperature for approximately 2 minutes, and the volume was observed to remain consistent. Rotary evaporation was continued in a water bath at 32° C., and the sample quickly evaporated, producing white solids. The sample was left on the rotary evaporator for approximately 4 hours. The resulting white/off-white solids were scraped and were observed to be glassy. The sample was placed in a vacuum oven at ambient temperature for 1 day. Upon removal, cracked, glassy, non-birefringent solids were observed. The XRPD pattern was obtained for the 1:1 Δ$^9$-THC/trimethyl-β-cyclodextrin (TOMBC) powder showing amorphous halos (FIG. 31)

Example 6: Solid Δ$^9$-THC Compositions by Lyophilization (Ratio Study)

A commercially available Δ$^9$-THC-acetonitrile solution (Cayman Chemical), approximately 50 mg Δ$^9$-THC per mL, was used. The actual concentration was determined gravimetrically by taring a vial and recording its weight, adding 1 mL of solution, evaporating the solution, vacuum drying the sample at room temperature for 12 hours and reweighing the vial. The actual concentration was determined to be 51 mg/mL. Into 1 dram vials, 300 μl of the Δ$^9$-THC acetonitrile solution was dispensed and allowed to evaporate at room temperature resulting in each vial containing ca. 15.3 mg of Δ$^9$-THC.

Δ$^9$-THC (ca. 15.3 mg) was dissolved in dioxane (3 mL solvent used) and transferred into a 25 mL round bottom flask. The powder former (amount based on 1:1, 1:2, 1:4, 2:1 or 4:1 molar Δ$^9$-THC:powder former ratio) was dissolved H$_2$O (2 mL) and, if needed, dioxane (2 mL) was added to form a solution. The powder former solution was added to the Δ$^9$-THC solution in the round bottom flask. The round bottom flask was then submerged in a dry ice/acetone bath to freeze the solution while continuously rotating the flask by hand to maximize surface area and form an even, thin layer around the flask. Once frozen, the round bottom flask was attached to a LabConco lyophilizer with an Edwards RV8 vacuum pump pre-equilibrated at ~−50° C. Samples were left overnight (18 hrs) and removed the next day.

Δ$^9$-THC and powder formers (aspartame, caffeine and L-valine) were lyophilized using the described procedure to determine if a flowable powder would result. A sampling of the Δ$^9$-THC flowable powders were stored at sub-ambient temperatures (~−18° C.) for 7 days and observed to see if a flowable powder remained. A sampling of the Δ$^9$-THC flowable powders were then left at ambient temperature for 7 days and again observed to see if a flowable powder remained. These results are shown in Table 3.

TABLE 3

| Powder former | THC:PF ratio | Flowable after lyophilization | Flowable after storage at −18° C. (7 days) | Flowable after storage at ambient temperature (7 days) |
|---|---|---|---|---|
| Aspartame | 1:1 | Yes | Yes | Yes - Cream color |
|  | 1:2 | Yes | Yes | Yes - Off-white color |
|  | 1:4 | Yes | Yes | Yes - Off-white color |
|  | 2:1 | Yes | Yes | Yes - Cream color |
|  | 4:1 | Yes | Yes | Yes - Yellow color |
| L-Valine | 1:1 | Yes | Yes | Yes - Off-white color |
|  | 1:2 | Yes | Yes | Yes - Off-white color |
|  | 1:4 | Yes | Yes | Yes - White color |
|  | 2:1 | Yes | Yes | Yes - Cream color |
|  | 4:1 | Yes | Yes | Yes - Tan color |
| Caffeine | 1:1 | Yes | Yes | Yes - Tan color |
|  | 1:2 | Yes | Yes | Yes - Cream color |
|  | 1:4 | Yes | Yes | Yes - White color |
|  | 2:1 | No | No | No - Yellow color |
|  | 4:1 | No | No | No - Orange brown color |

The flowable powders were characterized using a Rigaku Smart-Lab X-ray diffraction system and their X-ray powder diffraction (XRPD) patterns are shown in FIGS. 32-41.

Example 7: Solid Δ$^9$-THC Compositions by Lyophilization (Humidity Study)

A commercially available Δ$^9$-THC acetonitrile solution (Cayman Chemical), approximately 50 mg Δ$^9$-THC per mL, was used. The actual concentration was determined gravimetrically by taring a vial and recording its weight, adding 1 mL of solution, evaporating the solution, vacuum drying the sample at room temperature for 12 hours and reweighing the vial. The actual concentration was determined to be 51 mg/mL. Into 1-dram vials, 1,000 µl of the $\Delta^9$-THC acetonitrile solution was dispensed and allowed to evaporate at room temperature resulting in each vial containing ca. 50 mg of $\Delta^9$-THC. For each of the following experiments, four 1-dram vials were used totally approximately 200 mg of $\Delta^9$-THC.

7.1 Scaled up 1:1$\Delta^9$-THC: aspartame powder: $\Delta^9$-THC (~200 mg) was dissolved in 1,4-dioxane (8-12 mL of solvent used) and transferred to a 50 mL round bottom flask. In a separate vial, aspartame (1 molar equivalent, 187.3 mg) was dissolved with dioxane and water. The aspartame solution was added to the $\Delta^9$-THC solution in the round bottom flask. The round bottom flask was then submerged in liquid nitrogen to freeze the solution while continuously rotating the flask by hand in order to maximize surface area and form an even, thin layer around the flask. Once frozen, the round bottom flask was attached to a LabConco lyophilizer with an Edwards RV8 vacuum pump pre-equilibrated at ~−50° C. The sample was left overnight and removed the next day.

7.2 Scaled up 1:1$\Delta^9$-THC: L-Valine powder: $\Delta^9$ THC (~200 mg) was dissolved in 1,4-dioxane (8-12 mL of solvent used) and transferred to a 50 mL round bottom flask. In a separate vial, L-valine (1 molar equivalent, 74.5 mg) was dissolved with dioxane and water. The valine solution was added to the $\Delta^9$-THC solution in the round bottom flask. The round bottom flask was then submerged in liquid nitrogen to freeze the solution while continuously rotating the flask by hand in order to maximize surface area and form an even, thin layer around the flask. Once frozen, the round bottom flask was attached to a LabConco lyophilizer with an Edwards RV8 vacuum pump pre-equilibrated at ~−50° C. The sample was left overnight and removed the next day.

7.3 Scaled up 1:1$\Delta^9$-THC: Caffeine powder: $\Delta^9$ THC (~200 mg) was dissolved in 1,4-dioxane (8-12 mL of solvent used) and transferred to a 50 mL round bottom flask. In a separate vial, caffeine (1 molar equivalent, 123.4 mg) was dissolved with dioxane and water. The caffeine solution was added to the $\Delta^9$-THC solution in the round bottom flask. The round bottom flask was then submerged in liquid nitrogen to freeze the solution while continuously rotating the flask by hand in order to maximize surface area and form an even, thin layer around the flask. Once frozen, the round bottom flask was attached to a LabConco lyophilizer with an Edwards RV8 vacuum pump pre-equilibrated at ~−50° C. The sample was left overnight and removed the next day.

Each scaled up two-component mixture was then subsampled and stressed at various humidity conditions. Materials were visually examined and poured for flowability after 1 day, 3 days, 7 days, and 28 days. Humidity stress data of the flowable powders are shown in Table 4.

TABLE 4

| $\Delta^9$-THC:Powder former (1:1 mol:mol) | Relative Humidity (RH) | Timepoint (days) | Observations |
|---|---|---|---|
| Aspartame | 0% | 1 day | Flowable, white color |
| | | 3 days | Flowable, white color |
| | | 7 days | Flowable, white color |
| | | 28 days | Flowable, white color |
| | 45% | 1 day | Flowable, white color |
| | | 3 days | Flowable, white color |
| | | 7 days | Flowable, white color |
| | | 28 days | Flowable, white color |
| | 75% | 1 day | Flowable, white color |
| | | 3 days | Flowable, white color |
| | | 7 days | Flowable, white color |
| | | 28 days | Flowable, white color |
| | 95% | 1 day | Flowable, white color |
| | | 3 days | Flowable, white color |
| | | 7 days | Flowable, white color |
| | | 28 days | Flowable, white color |
| L-Valine | 0% | 1 day | Flowable, off-white color |
| | | 3 days | Flowable, off-white color |
| | | 7 days | Flowable, off-white color |
| | | 28 days | Flowable, off-white color |
| | 45% | 1 day | Flowable, off-white color |
| | | 3 days | Flowable, off-white color |
| | | 7 days | Flowable, off-white color |
| | | 28 days | Flowable, off-white color |
| | 75% | 1 day | Flowable, off-white color |
| | | 3 days | Flowable, off-white color |
| | | 7 days | Flowable, off-white color |
| | | 28 days | Flowable, off-white color |
| | 95% | 1 day | Flowable, off-white color |
| | | 3 days | Flowable, off-white color |
| | | 7 days | Flowable, off-white color |
| | | 28 days | Flowable, off-white color |
| Caffeine | 0% | 1 day | Flowable, cream color |
| | | 3 days | Flowable, brown color |
| | | 7 days | Flowable, brown color |
| | | 28 days | Flowable, dark brown color |
| | 45% | 1 day | Flowable, cream color |
| | | 3 days | Flowable, cream color |
| | | 7 days | Flowable, cream color |
| | | 28 days | Flowable, cream color |
| | 75% | 1 day | Flowable, cream color |
| | | 3 days | Flowable, orange color |
| | | 7 days | Flowable, orange color |
| | | 28 days | Flowable, orange color |
| | 95% | 1 day | Flowable, cream color |
| | | 3 days | Flowable, orange color |
| | | 7 days | Tacky, orange color |
| | | 28 days | Tacky, orange color |

The claimed invention is:

1. A solid $\Delta^9$-THC composition comprising $\Delta^9$-tetrahydrocannabinol (THC) and a powder former and having a molar ratio of $\Delta^9$-THC to powder former to form a flowable $\Delta^9$-THC powder and wherein the powder former is β-nicotinamide adenine dinucleotide and epigallocatechin gallate.

2. The solid $\Delta^9$-THC composition of claim 1, wherein the molar ratio of $\Delta^9$-THC to powder former ranges from about 4:1 to about 1:4, ranges from about 3:1 to about 1:3, ranges from about 2:1 to about 1:2 or is about 1:1.

3. A method of making a solid $\Delta^9$-tetrahydrocannabinol (THC) composition comprising the step of combining $\Delta^9$-THC with a powder former under conditions and in a molar ratio to form a flowable $\Delta^9$-THC powder, wherein the powder former is β-nicotinamide adenine dinucleotide and epigallocatechin gallate.

4. The method of making a solid $\Delta^9$-THC composition of claim 3 comprising the steps of: dissolving the $\Delta^9$-THC and the powder former in a solvent system to form a solution, and removing the solvent from the solution to yield a solid $\Delta^9$-THC composition.

5. The method of claim 4, wherein the dissolving step comprises the steps of: dissolving the $\Delta^9$-THC in a solvent system to form a $\Delta^9$-THC solution, dissolving the powder former in a solvent system to form a powder former solution, combining the $\Delta^9$-THC solution and the powder former solution to form a combined solution containing both $\Delta^9$-THC and the powder former compound, and removing the solvent from the combined solution to yield a solid $\Delta^9$-THC composition.

6. The method of claim 3, wherein the molar ratio of $\Delta^9$-THC to powder former ranges from about 4:1 to about 1:4, ranges from about 3:1 to about 1:3, ranges from about 2:1 to about 1:2 or is about 1:1.

7. The method of claim 3, wherein the $\Delta^9$-THC is synthetic $\Delta^9$-THC.

8. The method of claim 3, wherein the $\Delta^9$-THC is extracted $\Delta^9$-THC.

9. The method of claim 4, wherein the solvent is removed from the solution by lyophilization or by evaporation.

10. The method of claim 5, wherein the solvent is removed from the solution by lyophilization or by evaporation.

11. A pharmaceutical or nutraceutical composition comprising a solid $\Delta^9$-THC composition of claim 1 and a pharmaceutically- or nutraceutically-acceptable carrier, wherein $\Delta^9$-THC is present in the composition in a pharmaceutically or nutraceutically effective amount.

12. A method of treating a disease, disorder, or condition comprising the step of administering to a patient in need thereof a therapeutically effective amount of a solid $\Delta^9$-THC composition according to claim 1.

13. A method of treating a disease, disorder, or condition comprising the step of administering to a patient in need thereof a therapeutic composition containing a solid $\Delta^9$-THC composition according to claim 11.

14. A food or beverage product comprising a solid $\Delta^9$-THC composition of claim 1.

* * * * *